US010927333B2

(12) United States Patent
Zahn et al.

(10) Patent No.: US 10,927,333 B2
(45) Date of Patent: Feb. 23, 2021

(54) HIGH THROUGHPUT, FEEDBACK-CONTROLLED ELECTROPORATION MICRODEVICE FOR EFFICIENT MOLECULAR DELIVERY INTO SINGLE CELLS

(71) Applicant: Rutgers, The State University of New Jersey, New Brunswick, NJ (US)

(72) Inventors: Jeffrey Zahn, Princeton, NJ (US); Mingde Zheng, Highland Park, NJ (US); David I. Shreiber, Whitehouse Station, NJ (US); Hao Lin, Piscataway, NJ (US); Jerry W. Shan, Piscataway, NJ (US)

(73) Assignee: RUTGERS, THE STATE UNIVERSITY OF NEW JERSEY, New Brunswick, NJ (US)

(*) Notice: Subject to any disclaimer, the term of this patent is extended or adjusted under 35 U.S.C. 154(b) by 150 days.

(21) Appl. No.: 15/757,566

(22) PCT Filed: Sep. 2, 2016

(86) PCT No.: PCT/US2016/050201
§ 371 (c)(1),
(2) Date: Mar. 5, 2018

(87) PCT Pub. No.: WO2017/040995
PCT Pub. Date: Mar. 9, 2017

(65) Prior Publication Data
US 2018/0258379 A1     Sep. 13, 2018

Related U.S. Application Data

(60) Provisional application No. 62/214,665, filed on Sep. 4, 2015.

(51) Int. Cl.
    *B01L 3/00*     (2006.01)
    *C12M 1/42*     (2006.01)
    (Continued)

(52) U.S. Cl.
    CPC ......... *C12M 1/42* (2013.01); *B01L 3/502715* (2013.01); *B01L 3/502761* (2013.01);
    (Continued)

(58) Field of Classification Search
    CPC .......... C12M 1/42; C12M 1/00; C12M 23/16; C12M 23/02; C12M 23/00;
    (Continued)

(56) References Cited

U.S. PATENT DOCUMENTS 6,403,348 B1    6/2002   Rubinsky et al.
7,338,796 B1 *   3/2008   Davalos ............... B01F 5/0475
                                         422/81

(Continued)

FOREIGN PATENT DOCUMENTS

JP          H07184686 A      7/1995
JP          2008545415 A     12/2008
WO     WO 2006/112870 A1 * 10/2006 .............. C12M 3/00

OTHER PUBLICATIONS

Geng, et al: "Microfluidic Electroporation for Cellular Analysis and Delivery", National Institutes of Health, Oct. 7, 2013, Lab Chip, vol. 13, No. 19, pp. 3803-3821.

(Continued)

*Primary Examiner* — Christine T Mui
(74) *Attorney, Agent, or Firm* — Fox Rothschild LLP

(57) ABSTRACT

Systems and methods for cell electroporation and molecular delivery using an intelligent, feedback controlled, microscale electroporation system for transfecting single cells.

19 Claims, 20 Drawing Sheets

(51) Int. Cl.
  *C12N 13/00* (2006.01)
  *G01N 15/10* (2006.01)
  *C12M 3/06* (2006.01)

(52) U.S. Cl.
  CPC ............ *C12M 23/16* (2013.01); *C12M 35/02* (2013.01); *C12N 13/00* (2013.01); *G01N 15/1031* (2013.01); *G01N 15/1056* (2013.01); *B01L 2200/0647* (2013.01); *B01L 2300/0645* (2013.01); *G01N 2015/1006* (2013.01)

(58) Field of Classification Search
  CPC .. B01L 3/502715; B01L 3/5027; B01L 3/502; B01L 3/50; B01L 3/00
  USPC .......................................................... 422/76
  See application file for complete search history.

(56) References Cited

U.S. PATENT DOCUMENTS

| | | |
|---|---|---|
| 2004/0039327 A1 | 2/2004 | Miklavcic et al. |
| 2005/0048651 A1 | 3/2005 | Ryttsen et al. |
| 2008/0105565 A1 | 5/2008 | Davalos et al. |
| 2009/0029407 A1 | 1/2009 | Gazit et al. |
| 2010/0008780 A1 | 1/2010 | Miocevich |
| 2010/0068780 A1 | 3/2010 | Abonnenc et al. |
| 2012/0135887 A1 | 5/2012 | Lee et al. |

OTHER PUBLICATIONS

Zhu, et al: "Electroporation Based on Hydrodynamic Focusing of Microfluidiics with Low DC Voltage", Biomed Microdevices Feb. 2010, vol. 12, No. 1, pp. 35-40.

\* cited by examiner (a)

(b)

HIGH THROUGHPUT, FEEDBACK-CONTROLLED ELECTROPORATION MICRODEVICE FOR EFFICIENT MOLECULAR DELIVERY INTO SINGLE CELLS

CROSS REFERENCE TO RELATED APPLICATIONS

This application claims priority to U.S. application Ser. No. 62/214,665, filed Sep. 4, 2015, which is incorporated herein by reference in its entirety.

STATEMENT REGARDING FEDERALLY SPONSORED RESEARCH

The present invention was partly sponsored by the National Science Foundation (NSF) through the IDBR Award #1959918 and the CBET Award #0967598.

FIELD OF THE DISCLOSURE

The present disclosure relates to the field of cell electroporation and molecular delivery in general, using an intelligent, feedback-controlled, microscale electroporation system for transfecting single cells in a continuous-flow fashion.

BACKGROUND OF THE INVENTION

Delivery of small and macromolecules—including, for example, DNA, drug molecules, imaging agents, peptides, antibodies, and enzymes—into cells is critical to realizing their full potential in a range of research and therapeutic applications; yet, intracellular delivery and transfection remain difficult tasks. Successful transfection is a rate-limiting step in many types of biomedical research and bioproduction workflows that govern markets including biopharmaceuticals, RNA interference screening, and stem cell research. However, this potential has not been realized, largely because of the difficulties in safely, effectively, and efficiently transfecting the cells. The challenges include variable and poor transfection efficiency, especially with hard-to-transfect cell lines such as primary cell lines and stem cell lines that are of significant interest for studies of developmental dynamics, drug discovery, and regenerative medicine.

During electroporation, genes or other macromolecules are mixed with the live cells in a buffer medium and short pulses of high electric fields are applied. The cell membranes are transiently made porous and the genes or macromolecules enter the cells. However, electroporation frequently falls short of the desired efficiency and reliability, largely because of two deficiencies. First, the mechanisms that govern molecular transport following electroporation have been poorly understood. Second, the permeabilization threshold varies for different cells within a population and for different kinds of cells, as does the ability of these cells to survive permeabilization because of over-exposure to electrical signals. Furthermore, since the procedure is performed in large populations of cells whose properties vary among the individual cells in the population, the electroporation conditions can only be selected to address the average qualities of the cell population; the procedure as currently practiced cannot be adapted to the specific characteristics of individual cells, as well as customized for high throughput and automation at the same time.

Hence, there exists a need for a new and improved microfluidic electroporation device that can address the above challenges.

SUMMARY OF THE INVENTION

In one aspect, the present invention provides a system for electroporating a biological cell, the system comprising: a microfluidic channel adapted to receive a flow of a plurality of biological cells in a buffer solution, wherein the microfluidic channel comprises a detection area; a pair of electrodes adapted to apply an electrical field across the detection area; a signal generator unit, wherein the signal generator unit is capable of generating a cell detection signal and a permeabilization signal through the electrodes; a sensing unit, wherein the sensing unit is adapted to detect the impedance of the detection area; and a controller unit, wherein the controller unit is adapted to control the signal generator unit according to the impedance detected by the sensing unit.

In one embodiment, the signal generator unit is capable of generating the cell detection signal and the permeabilization signal simultaneously. In another embodiment, signal generator unit is capable of generating alternating current (AC) waveforms and a single or sequences of direct current (DC) pulse waveforms. In one embodiment, the signal generator unit is capable of generating a low amplitude sine-wave-based sensory electrical field across the pair of electrodes. In one embodiment, the signal generator unit is capable of generating single and sequences of DC pulses.

In one embodiment, the sensing unit comprises a lock-in amplifier. In another embodiment, the sensing unit is capable of resolving both the cell detection signal and the permeabilization signal simultaneously. In another embodiment, the sensing unit further comprises an imaging device capable of measuring the fluorescence of a cell within the detection area.

In one embodiment, the microfluidic channel is capable of hydrodynamically centering the flow of a plurality of biological cells through the detection area. In another embodiment, the system further comprises a second microfluidic channel adapted to receive a flow of buffer, and wherein the second microfluidic channel comprises a second detection area. In one embodiment, the sensing unit is adapted to detect the impedance of the second detection area.

In one embodiment, the signal generator unit is capable of generating a delivery signal. In one embodiment, the controller unit controls the signal generator unit to generate the permeabilization signal according to the impedance detected by the sensing unit. In another embodiment, the controller unit controls the signal generator unit to stop generation of the permeabilization signal and generate the delivery signal according to the impedance detected by the sensing unit.

In another aspect, the present invention provides a method for electroporating a biological cell in a buffer solution, the method comprising hydrodynamically focusing the biological cell to a detection area; generating a first electrical signal; monitoring the impedance value of the detection area using the first electrical signal, wherein an increase in impedance value of the detection area over a baseline threshold indicates the presence of the biological cell; generating, in response to an increase in impedance of the detection area, a second electrical signal; determining whether the impedance value of the detection area is greater than a permeabilization threshold value; and adjusting at least one parameter of the second pulse signal in response to the determining the impedance value of the detection area.

In one embodiment, the first electrical signal comprises a continuous low-amplitude sine waveform. In another embodiment, the second electrical signal comprises a DC pulse waveform, wherein the DC pulse waveform comprises one pulse or multiple pulses at a defined frequency.

In one embodiment, the method further comprises stopping the second electrical signal in response to determining that the measured impedance value is about equal to the permeabilization threshold value; and generating a third electrical signal, wherein the third electrical facilitates delivery of a molecule into the cell focused within the detection area. In another embodiment, the method further comprises determining whether the impedance value of the detection area is about equal to the permeabilization threshold value; and adjusting at least one parameter of the third electrical signal in response to determining the impedance value of the detection area is not about equal to the permeabilization threshold value.

In one embodiment, the method further comprises stopping the third electrical signal in response to determining the impedance value of the detection area is one of: less than or equal to a viability threshold, or equal to the baseline threshold. In one embodiment, the third electrical is stopped in response to determining that the impedance value of the detection area is less than or equal to the viability threshold. In another embodiment, the third electrical signal is stopped in response to determining that the impedance value of the detection area is equal to the baseline threshold.

In one embodiment, the baseline threshold is determined by continuously monitoring the impedance value of a second detection area through which only a buffer solution is flowing.

In one embodiment, the at least one parameter of the second electrical signal is selected from the group of: electric field amplitude, pulse duration, pulse train frequency, duty cycle, and number of cycles. In another embodiment, the at least one parameter of the third electrical signal is selected from the group of: electric field amplitude, pulse duration, pulse train frequency, duty cycle, and number of cycles.

In one embodiment, the permeabilization threshold value is determined experimentally. In another embodiment, the permeabilization threshold value is determined using a mathematical model. In one embodiment, the permeabilization threshold value corresponds to an optimal cell permeabilization that does not cause cell death.

In a another aspect, the present invention provides a method for electroporating a plurality of biological cells, the method comprising hydrodynamically focusing a continuous flow of a plurality of biological cells into a single-file flow, wherein the single-file flow passes each of the plurality of biological cells through a detection area; generating a first electrical signal; monitoring the impedance value of the detection area using the first electrical signal, wherein an increase in impedance value of the detection area over a baseline threshold indicates the presence of each of the plurality of biological cells; generating, in response to an increase in impedance of the detection area, a second electrical signal; determining whether the impedance value of the detection area is greater than a permeabilization threshold value; adjusting at least one parameter of the second pulse signal in response to the determining the impedance value of the detection area.

In one embodiment, the method further comprises stopping the second electrical signal in response to determining that the measured impedance value is about equal to the permeabilization threshold value; and generating a third electrical signal, wherein the third electrical signal causes delivery of a molecule into each of the plurality of biological cells focused within the detection area. In another embodiment, the method further comprises determining whether the impedance value of the detection area is about equal to the permeabilization threshold value; and adjusting at least one parameter of the third electrical signal in response to determining the impedance value of the detection area is not equal to the permeabilization threshold value.

In one embodiment, the method further comprises stopping the third electrical signal in response to determining the impedance value of the detection area is one of: less than or equal to a viability threshold, or equal to the baseline threshold. In one embodiment, the third pulse is stopped in response to determining the impedance value of the detection area is less than or equal to the viability threshold. In another embodiment, the third electrical signal is stopped in response to determining the impedance value of the detection area is about equal to the baseline threshold.

In one embodiment, the baseline threshold is determined by continuously monitoring the impedance value of a second detection area through which only a buffer solution is flowing.

In one embodiment, the at least one parameter of the second electrical signal is selected from the group of: electric field amplitude, pulse duration, pulse train frequency, duty cycle, and number of cycles. In another embodiment, the at least one parameter of the third electrical signal is selected from the group of: electric field amplitude, pulse duration, pulse train frequency, duty cycle, and number of cycles.

In one embodiment, the permeabilization threshold value is determined experimentally. In another embodiment, the permeabilization threshold value is determined using a mathematical model. In one embodiment, the permeabilization threshold value corresponds to an optimal cell permeabilization that does not cause cell death.

BRIEF DESCRIPTION OF THE DRAWINGS

Embodiments will be described with reference to the following drawing figures, in which like numerals represent like items throughout the figures, and in which.

DETAILED DESCRIPTION OF THE INVENTION

Figure 1A:
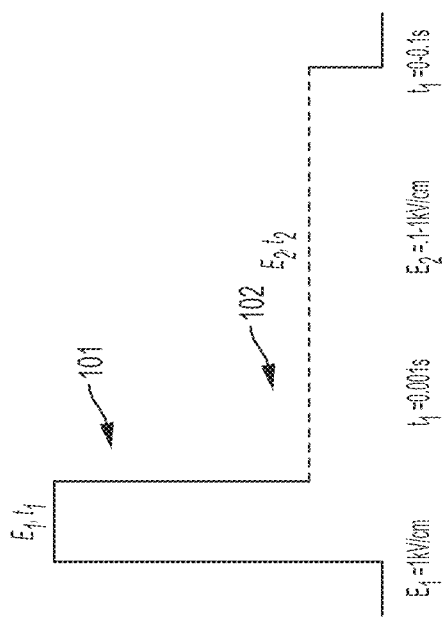
FIGS. 1A and 1B illustrate the schematics of the permeabilization and delivery electroporation signals, according to an embodiment.

Methods and systems are disclosed for cell electroporation and molecular delivery in using an intelligent, feedback controlled, microscale electroporation system for transfecting flowing single cells.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present disclosure may be embodied in other specific forms without departing from its spirit or essential characteristics. The described embodiments are to be considered in all respects as illustrative. The scope of the disclosure is, therefore, indicated by the appended claims.

Reference throughout this specification to features, advantages, or similar language does not imply that all of the features and advantages that may be realized with the present disclosure should be or are in any single embodiment of the disclosure. Rather, language referring to the features and advantages is understood to mean that a specific feature, advantage, or characteristic described in connection with an embodiment is included in at least one embodiment of the present disclosure. Thus, discussions of the features and advantages, and similar language, throughout the specification may, but do not necessarily, refer to the same embodiment.

Furthermore, the described features, advantages and characteristics of the disclosure may be combined in any suitable manner in one or more embodiments. One skilled in the relevant art will recognize, in light of the description herein, that the disclosure can be practiced without one or more of the specific features or advantages of a particular embodiment. In other instances, additional features and advantages may be recognized in certain embodiments that may not be present in all embodiments of the disclosure.

Reference throughout this specification to "one embodiment," "an embodiment," or similar language means that a particular feature, structure, or characteristic described in connection with the indicated embodiment is included in at least one embodiment of the present disclosure. Thus, the phrases "in one embodiment", "in an embodiment", and similar language throughout this specification may, but do not necessarily, all refer to the same embodiment.

As used in this document, the singular form "a", "an", and "the" include plural references unless the context clearly dictates otherwise. Unless defined otherwise, all technical and scientific terms used herein have the same meanings as commonly understood by one of ordinary skill in the art. As used in this document, the term "comprising" means "including, but not limited to".

Electroporation is a means to access the cytoplasm of a cell for delivery of molecules. In the technique, an electric field, which can be applied in vitro or in vivo, transiently permeabilizes the cell membrane through which biologically active molecules can enter the cell, such as DNA, RNA, and amino acids. The current disclosure describes a system and method for a flow-based, automated cell detection-and-electroporation signal system to detect and electroporate cells.

In one embodiment, the system of the present invention continuously monitors the current flowing across a detection area to determine the cell membrane impedance of a single cell flowing through a microfluidic channel before, during and after electroporation. The system further includes a sensing unit that may comprise a cell membrane permeabilization feedback control loop that monitors the impedance of a detection area of the microfluidic channel using a first electrical detection signal to determine when a single cell enters into the detection area. In an embodiment, the first electrical detection signal is an AC sine waveform of low amplitude. The single cell entering the detection area may be represented as a rise in impedance over a baseline threshold, resembling a pulse resistive sensor in, for example, a coulter counter. The application of a second electrical permeabilization signal permeabilizes the cell membrane of the single cell. The system may automatically adjust parameters of the second permeabilization signal until a predefined sub-lethal permeabilization threshold is met. The impedance of the detected cell is continuously monitored to determine when the sub-lethal permeabilization threshold is achieved. A third electrical delivery signal is applied to deliver molecules into the cell cytoplasm. The parameters of the third delivery signal may be automatically adjusted by the system. During this process, the impedance of the detection area and detected single cell may be continuously monitored to detect if the impedance change exceeds a predefined maximal threshold, which can cause possible irreversible cell damage, whereupon the feedback control loop turns off the third electric delivery signal and resets the system for the next passing cell. The thresholds described above may be selected from a database, comprising a data set of calibration results performed beforehand, and/or derived real time using computational models, based on the cell size and type of cell population of the detected cell.

In an embodiment, a pair of electrodes in a continuous-flow microchannel apply an AC sinewave of low amplitude to sense the impedance change in a detection area between the electrodes. Upon an increase in impedance due to the electrical current displacement from a passing cell, a signal generator unit outputs a DC pulse waveform to permeabilize the cell membrane of the cell. A sensing unit monitors the change in impedance of the cell as its membrane becomes more conducting due to the permeabilization of its membrane as a result of the permeabilizing DC pulse waveform. This membrane permeabilization is reflected as an electrical impedance readout which is being monitored and checked against a predetermined threshold to ensure that the impedance threshold associated with cell death for that particular cell has not been exceeded. A feedback loop monitors if the threshold is not exceeded, the permeabilizing DC pulse waveform is applied, and if the threshold is reached, the permeabilizing DC pulse waveform is stopped. A delivery DC pulse waveform is then applied to drive the exogenous molecules into the cell, it is of lower-amplitude compared to the membrane permeabilizing DC pulse waveform but longer in duration, in order to maintain the membrane opening and electrophoretically drive the delivery. During this process, the sensing unit remains on to continuously monitor the impedance of the cell to ensure the permeabilization readout has not exceeded the threshold which indicates imminent cell death.

As used herein, a signal is any time-varying waveform and may include, for example, an alternating current (AC) waveform or a direct current (DC) waveform. In some embodiments, a signal of the present invention may be an AC sinewave waveform, a single DC pulse waveform, or a series of DC pulse waveforms. In some embodiments, the first electrical detection signal may be an AC waveform. In other embodiments, the first electrical detection signal may be a series of DC pulse waveforms. In other embodiments, the second electrical permeabilization signal may be a DC pulse waveform or a series of DC pulse waveforms. In some embodiments, the third electrical delivery signal may be a DC pulse waveform or a series of DC pulse waveforms.

Figure 1B:
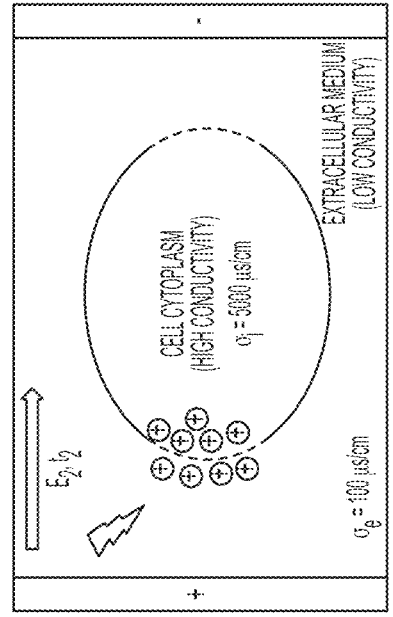
Figure 1B:
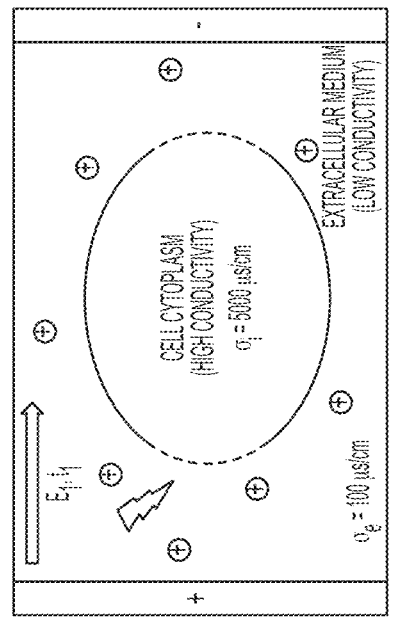

FIGS. 1A and 1B show the permeabilization signal and delivery signal as described above: a first signal 101 for permeabilization, followed in time by a second signal 102 for molecular delivery. The application of the first high field ("HV") signal is in general a necessary condition for membrane permeabilization, to overcome the critical threshold of the transmembrane potential. On the other hand, once permeabilization is achieved, a low field ("LV") signal can be employed to deliver the small and big molecules effectively while simultaneously decreasing damage due to field exposure. Hence, the two-signal electroporation system may be uniquely designed with the first signal being high amplitude, short duration which serves to permeabilize the cell membrane without irreversibly damaging the cells, and second signal being longer in duration and lower in amplitude serving to retain membrane pore opening and to electrophoretically drive molecules into cells. By utilizing a series of signals in this manner, cell electroporation and molecular transport efficiency are improved simultaneously with increased cell viability over known electroporation techniques. In the context of the overall automatic electroporation system, both the permeabilization signal and delivery signal may be monitored, executed and/or regulated by a controller unit comprising a central processing algorithm which governs when and how much to apply the aforementioned signals. The central processing algorithm may also be able to initiate or terminate either the permeabilization or delivery signals anytime during the cell membrane impedance monitoring period while the presence of the single cell under observation remains.

The electric field strength and duration may be tailored with respect to the target molecule to enhance overall performance, using techniques known to those skilled in the art. In some embodiments, the applied field strength of the permeabilization signal may range from 0.1 to 5 kV/cm with a duration between 0.1 and 100 ms. In another embodiment, the applied field strength of the delivery signal may range from 0.1 to 5 kV/cm with a duration between 0.1 and 100 ms. In an embodiment, the permeabilization signal is designed with the permeabilization signal high in amplitude (e.g., >1 kV/cm) but short in duration (e.g., <1 ms) to electropermeabilize the cell membrane; and the delivery signal low in amplitude (<0.6 kV/cm) but long in duration which serves to retain the opening of the pores from the first signal and electrophoretically transport molecules into the cell. For example, in an embodiment, for any chosen cell type that undergo such electroporation, the initial output amplitude and duration information of the two signals may be chosen based on set values known in literature and may be inputted by the operator prior to system execution. In some embodiments, the parameters for common cell types may be stored in the system. In other embodiments, dependent upon the sensory sweep of the cell membrane impedance information during the application of any of the two signals, the central control algorithm retains the ability to modify (e.g., change parameters such as amplitude, terminate or extend) either of the signals based on the continuous tracking/sweeping of the cell membrane state in order to preserve cell viability.

For example, in an embodiment, the first signal may be programmed at $V1=100$ V ($E1=100,000$ V/m) and $t1=0.001$ s in strength and duration at all times, respectively, to promote significant permeabilization with low delivery and high viability for different cell and molecule types. The second LV signal parameters may be programmed to target molecule's size and charge, cell type, and HV signal parameters. For example, in an embodiment, the second signal may be programmed at $1\sim10$V/m and $t1=0$-$0.1$ s in strength and duration. The electrical signal amplitude and duration values can also be automatically adjusted dynamically for working with various cell types at hand. In the context of the automated electroporation system, for any chosen cell type that undergo such electroporation, the operator has the option of allowing the system to determine the initial parameters for the permeabilization signal upon the detection of a single cell and its impedance reading by gradually increasing the amplitude from a base value such as 0 kV/cm electric field at or below a maximal increment rate of 10 kV/cm electric field per millisecond, until a cell membrane permeabilization indication signal is detected by the system. The electric field and duration of the first signal may be recorded and stored for use as a future reference for this type of cells.

Further, the application of the second signal may be based on the electric field strength of the first pulse, in which a signal with reduced electric field strength compared to the first signal may be used. For example, if a 1 kV/cm electric field strength was used to permeabilize the cell by the first signal, the system may initiate the second signal with a user-definable reduction such as 40% to output a pulse of 0.6 kV/cm electric field strength. Continuous tracking of the cell membrane state may also provide information regarding the cell viability, and the second signal may be terminated either based on the cell viability close to reaching a point of irreversible damage (threshold determined through pre-calibration) or saturation of the delivered materials (threshold determined through pre-calibration).

In an embodiment, the two-signal electroporation system may be designed to operate at a microscale level, and the two signals may be "chopped" into trains of DC pulses at adjustable frequencies (1 HZ-1 GHz, 0-100% duty cycles) with the appropriate amplitude adjustment to meet the permeabilization requirement, in order to measure the cell membrane permeabilization response during electroporation without the generation of electrolysis. In an embodiment, a database may be created comprising experimental characterization and/or computations modeling of the permeabilization signal based on cell type, structure, buffer characteristics, microfluidic channel characteristics, etc. As discussed below the signal may then be designed based on the detected cell and other properties using the database and/or computations modeling based on the database.

Figure 2A:
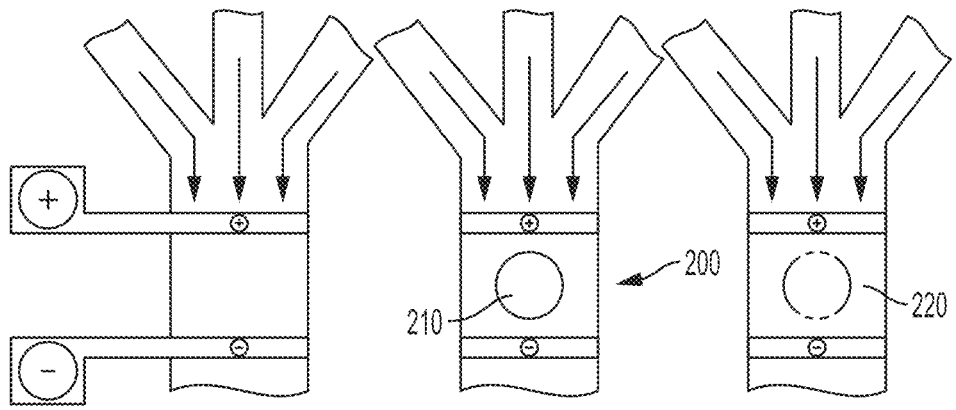
FIGS. 2A, 2B and 2C illustrate the change in impedance over time when a cell enters a detection area and when the cell is permeabilized, according to an embodiment.
Figure 2B:
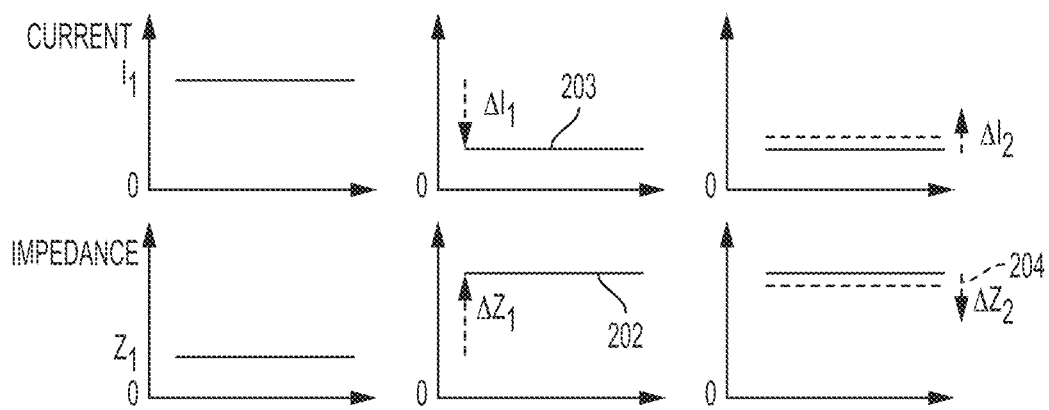
Figure 2C:
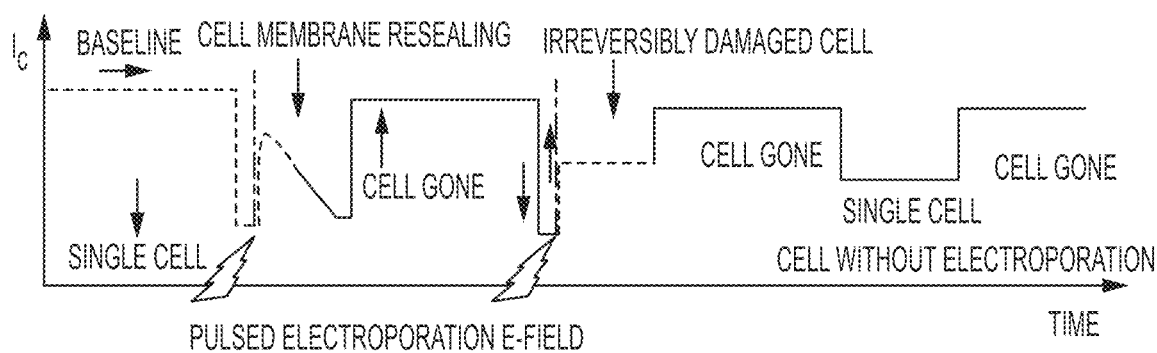

In some embodiments, the system of the present invention monitors the detection area of the microfluidic channel to detect a cell within the detection area of the microfluidic channel and monitors the permeabilization state of the detected cell via impedance monitoring. FIG. 2A and FIG. 2B illustrates the change in overall channel impedance as a cell moves through a microfluidic channel. An alternating current detection signal is applied across the microfluidic channel, and as the cell 210 is drawn through the microfluidic channel 200, it displaces the surrounding electrolyte causing a brief increase in electrical impedance under alternative current-based sensor detection 202 of the liquid (resembling resistive pulse), which is monitored through changes in electric current 203 across the channel, according to Ohm's law. This allows for enumeration of cells through the number of resistive pulses and sizing information based on the magnitude of the pulse, which in turn depends on the volume of displaced electrolyte. The increase in impedance occurs because the non-conducting, lipid bi-layer that comprises the cell membrane is intact and prevents open communication of the intracellular and intercellular solutions. However, once permeabilized 220, the cell becomes conductive, and the impedance drops 204 (and the electric current increases). The change in impedance may be detected to provide a signature of the permeabilization state of the cell as shown in FIG. 2, and the applied electric field may be dynamically adjusted to switch to a low-strength, well tolerated customized field for the specific cell type and size to maximize delivery, as described above. FIG. 2C illustrates a continuous flow process utilizing the impedance drops to detect cell entry and permeabilization using similar principles.

Figure 3A:
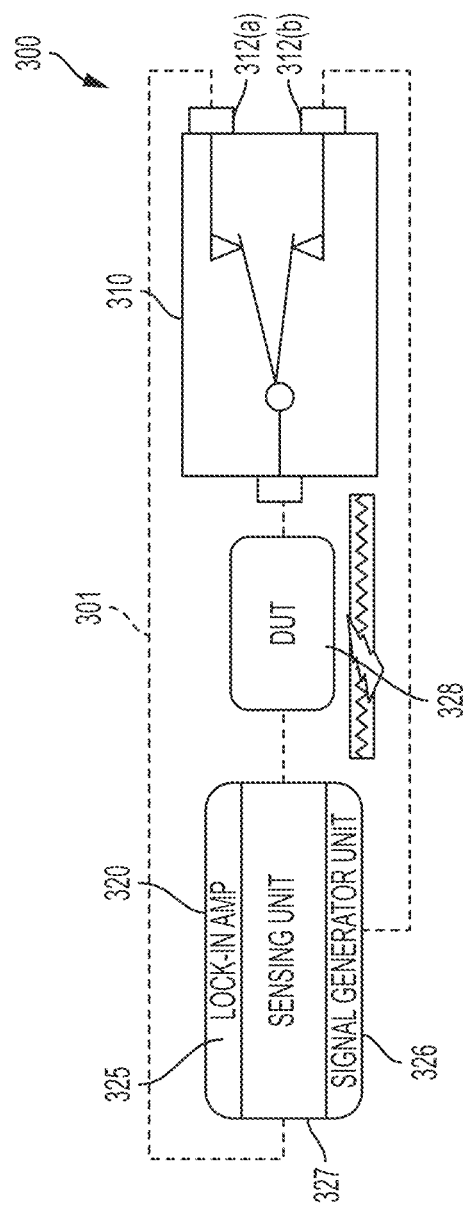
FIGS. 3A-3G illustrate schematics of the smart electroporation system, according to a plurality of embodiments.
Figure 3B:
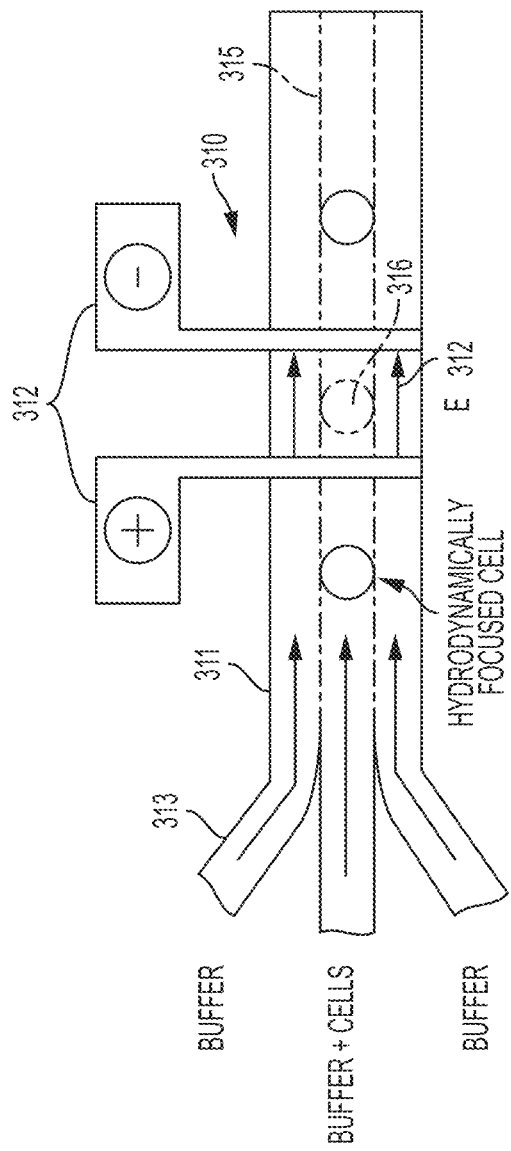
Figure 3C:
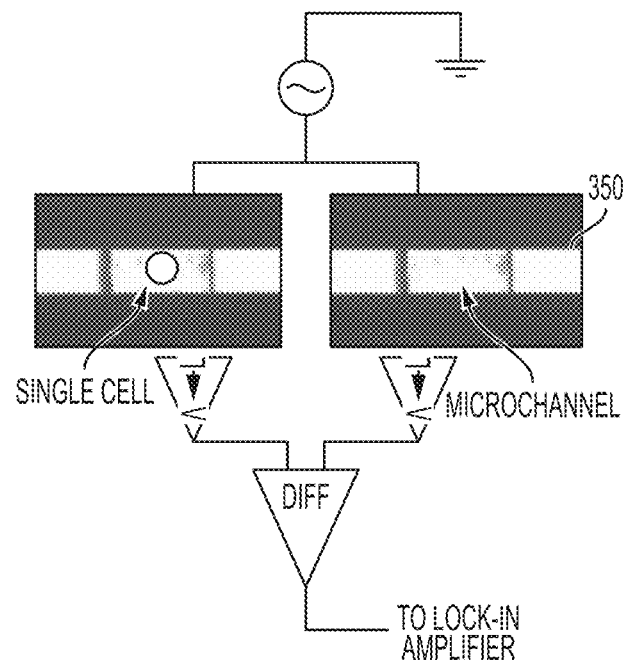

FIGS. 3A to 3C illustrate an embodiment of a "smart" electroporation system of the current disclosure that recognizes the permeabilization state of each cell and dynamically modulates the permeabilization signal to prevent over-exposure to high strength fields, and then applies a delivery signal that is specifically designed to drive the desired molecule(s) into the cell.

FIG. 3A provides a schematic of a smart electroporation system 300. The system may include a microfluidic cell handling system 310 that is integrated with an electrical permeabilization measurement apparatus 320 to form a fully autonomous, synchronized, impedance feedback-controlled micro-electroporation platform for permeabilizing different types of cells.

The microfluidic cell handling system 310 may comprise a microfluidic channel adapted to receive a flow of a plurality of biological cells in a buffer solution, wherein the microfluidic channel comprises a detection area. The electrical permeabilization apparatus 320 may comprise a pair of electrodes adapted to apply an electrical field across the detection area; a signal generator unit, wherein the signal generator unit is capable of generating a cell detection signal and a permeabilization signal through the electrodes; a sensing unit, wherein the sensing unit is adapted to detect the impedance of the detection area; and a controller unit, wherein the controller unit is adapted to control the signal generator unit according to the impedance detected by the sensing unit. In some embodiments, the impedance changes occurring in the cell membrane during electroporation are detected and monitored using a lock-in amplifier 325 and used it as an indicator of permeabilization. In an embodiment, the signal generator unit may comprise one or more electrical signal generators. In some embodiment, the signal generator unit may comprise an electrical recording apparatus integrated with the one or more electrical signal generators, and a controller unit (not shown here) may be programmed to dynamically modulate signal parameters using the cell impedance feedback information according to a central processing algorithm. In an embodiment, the electrical permeabilization apparatus 320 may utilize a feedback control loop 301 to transmit a signal feedback control signal generated by the controller unit to the electrodes 312(a) and 312(b) for modulating the duration and magnitude of the signals based on the severity of the impedance changes, in order to improve molecular delivery and cell viability. In an embodiment, the controller unit may utilize the impedance readings from the lock-in amplifier 325 and the signal characteristics from the signal generator unit 326 to generate the control signal. The signal generator unit may be used to generate signals and/or communicate with the electrodes via the feedback loop. The permeabilization apparatus 320 may also include a sensing unit 327 for analyzing and deciding the threshold for permeabilization. The permeabilization apparatus 320 may also include a DUT 328 a closed microfluidic channel of various designs that permits single cell flow through a confined space to allow recognizable or enhanced cell overall impedance or membrane permeabilization signal.

The cell handling system 310 may include a microfluidic device 311 designed to hydrodynamically-focus single cells in a defined detection area 312. A signal may only be applied by the smart electroporator upon detection of a cell within the detection area 312, and the cell membrane impedance may be monitored and compared to various threshold values such as a baseline threshold, indicating no cell is present in the detection area, a sub-lethal permeabilization threshold that maximizes efficiency and cell viability, and a maximal permeabilization threshold beyond which cell viability decreases below an acceptable amount. The threshold values for the electroporation apparatus and cell type may be established in advance, during calibration, to prevent over-electropermeabilization, or determined in real-time during use. The system may be configured to apply, terminate, or alter the various signals once the threshold conditions have been met.

FIG. 3B illustrates a microfluidic cell handling system 310 of a smart electroporation system, according to an embodiment. The system may be designed using microfabrication techniques known to those skilled in the art. As shown in FIG. 3B., the microfluidic channels 313 may be patterned on the glass slides using techniques such as lithography, and may be configured for hydrodynamically focusing (using a fluid microchannel 315) a single cell 316 for delivery between the electrodes. Hydrodynamically focusing the cells into single-file using fluid streams from side inlets permits continuous cell introduction, and is preferred over a narrow single channel because of the propensity for those channels to clog. Cell concentrations and flow rates may be controlled to provide optimal spacing between cells. In an embodiment, electrodes 312(a) and 312(b) are fabricated using liftoff techniques on clean glass slides, and may be used for co-planar sensing, permeabilizing cells, and delivering the transport-promoting electric field. In an example embodiment, the electrodes are patterned using a lithographically defined photoresist masking layer (EVG620 Exposure system) to define the electrode areas, followed by sputtering a 1000 Å thick Ti/Pt layer (Kurt J. Lesker PVD75) and photoresist removal in acetone solution. The microfluidic channels are fabricated using standard soft lithography, where a lithographically patterned SU-8 negative photoresist (Microchem, Newton, Mass.) serves as a negative template for microchannel replica molding. A poly(dimethyl siloxane) (PDMS) (Dow Corning, Midland, Mich.) solution is poured over the master and baked at 60° C. to produce a negative relief. The PDMS is peeled from the master and holes are punched for inlets and outlets. The PDMS and sputtered glass slide are treated with oxygen plasma to activate the surfaces and bonded together with feature alignment. The microchannels may be 1 cm long, 150 μm wide, and 10 μm deep. A pair of microelectrodes with a spacing of 120-400 μm is defined at a designated location along each microchannel. The inlets are connected to a syringe pump (Harvard Apparatus, Cambridge, Mass.) using polyethylene tubing (Small Parts, Miami Lakes, Fla.) for cell and sample introduction. Conductive epoxy (Circuit Works, Inc., Somerville N.J.) is used to fuse the exposed electrode pads with copper wires, allowing connection with external electronics.

As shown in FIG. 3C, in an embodiment, the system may also include a second, identical microchannel 350 with electrodes. The second, identical microchannel may be flowing with a buffer solution but no cells, and the impedance value of the second, identical microchannel may be sampled in parallel to the first microchannel through which cells are flowing to provide an ideal reference signal for differentiation and aid in detecting fast-moving, single cells. The microelectrodes from each of the two microchannels may each be connected to a current-to-voltage converter 318(a) and 318(b), which are in turn connected to a lock in amplifier 325.

The system may also include an imaging device (e.g., a fluorescent imaging device) capable of imaging the permeabilization stage and the delivery stage of the smart electroporation system. For example, a Cooke scientific CMOS camera may be used, which is capable of capturing full field (2560×2160 pixels) epifluorescent images at 100 fps and a partial field (100×2160) at close to 2000 fps. The camera will be triggered to capture epifluorescent images during the time the cell is within the electrodes.

Figure 3D:
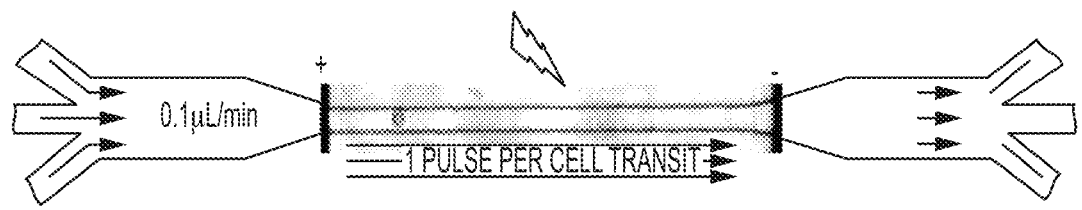
Figure 3E:
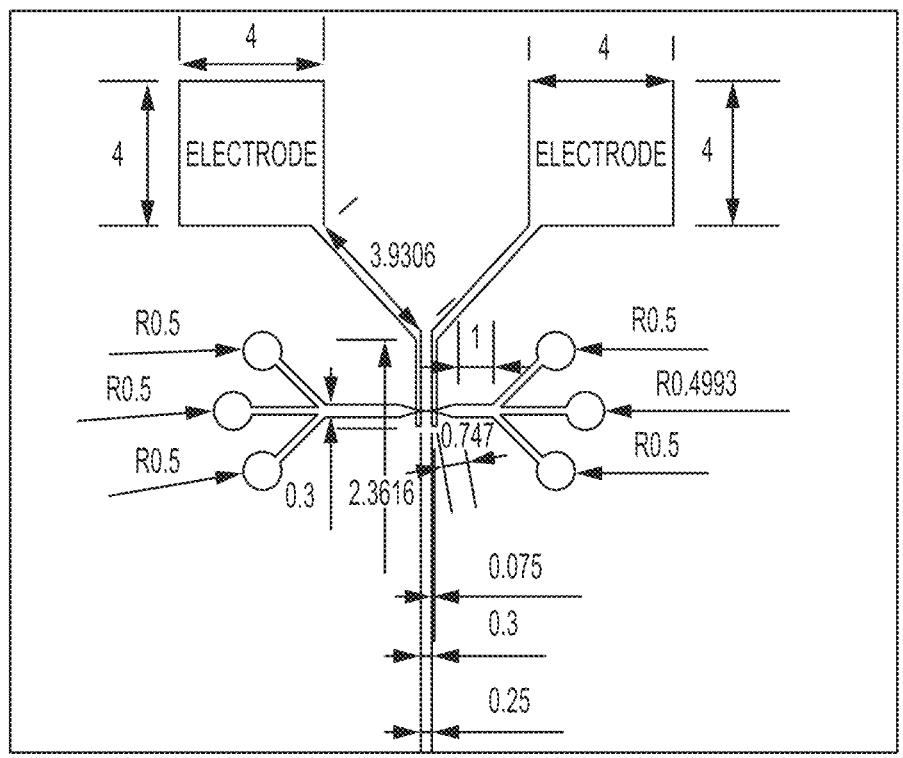
Figure 3F:
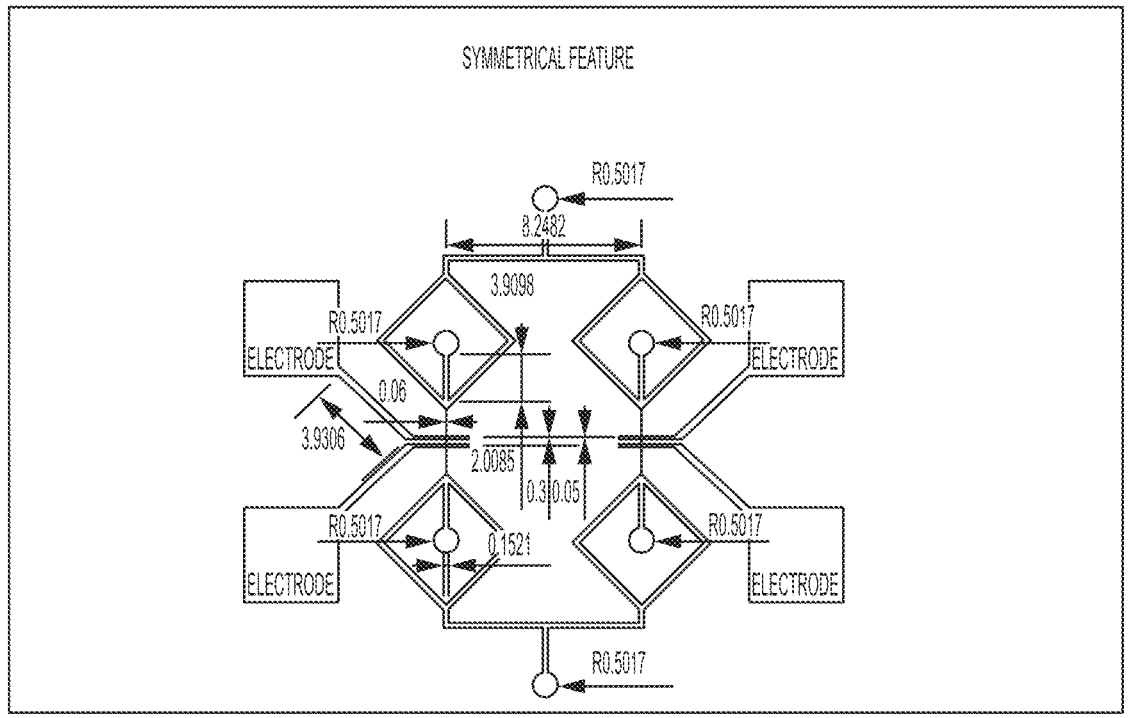
Figure 3G:
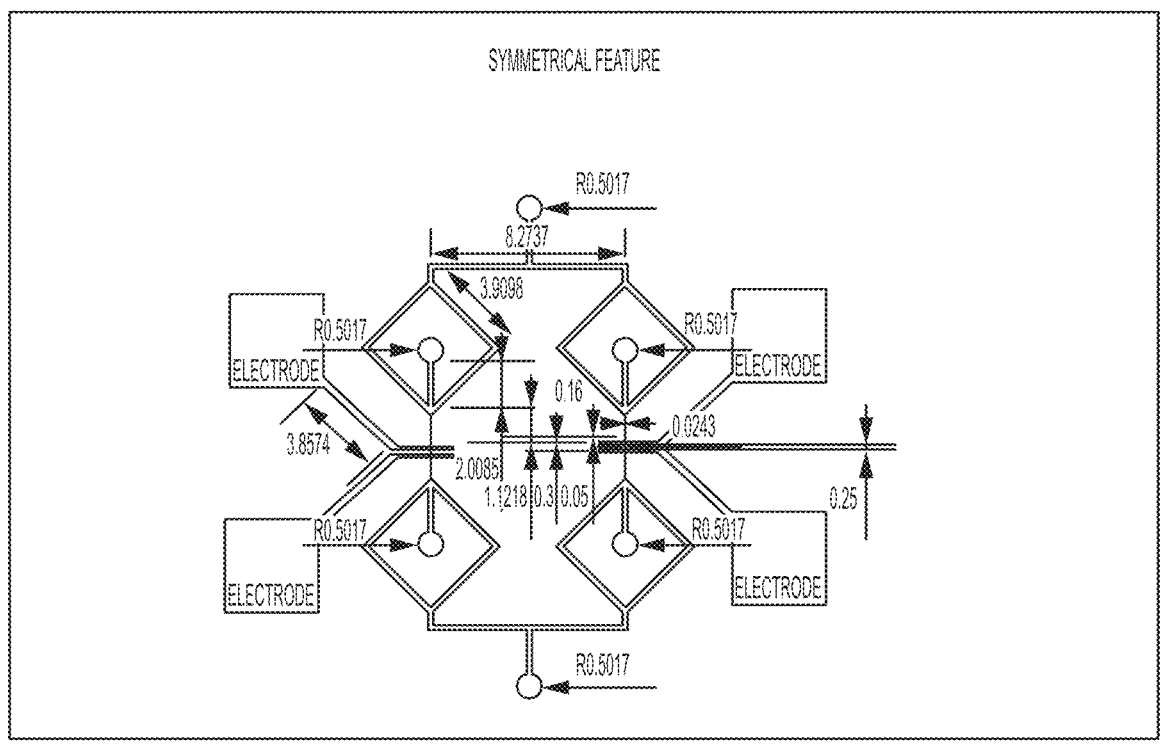

FIGS. 3E-3G illustrate various embodiments of the smart electroporation system in accordance with the current disclosure.

Figure 4A:
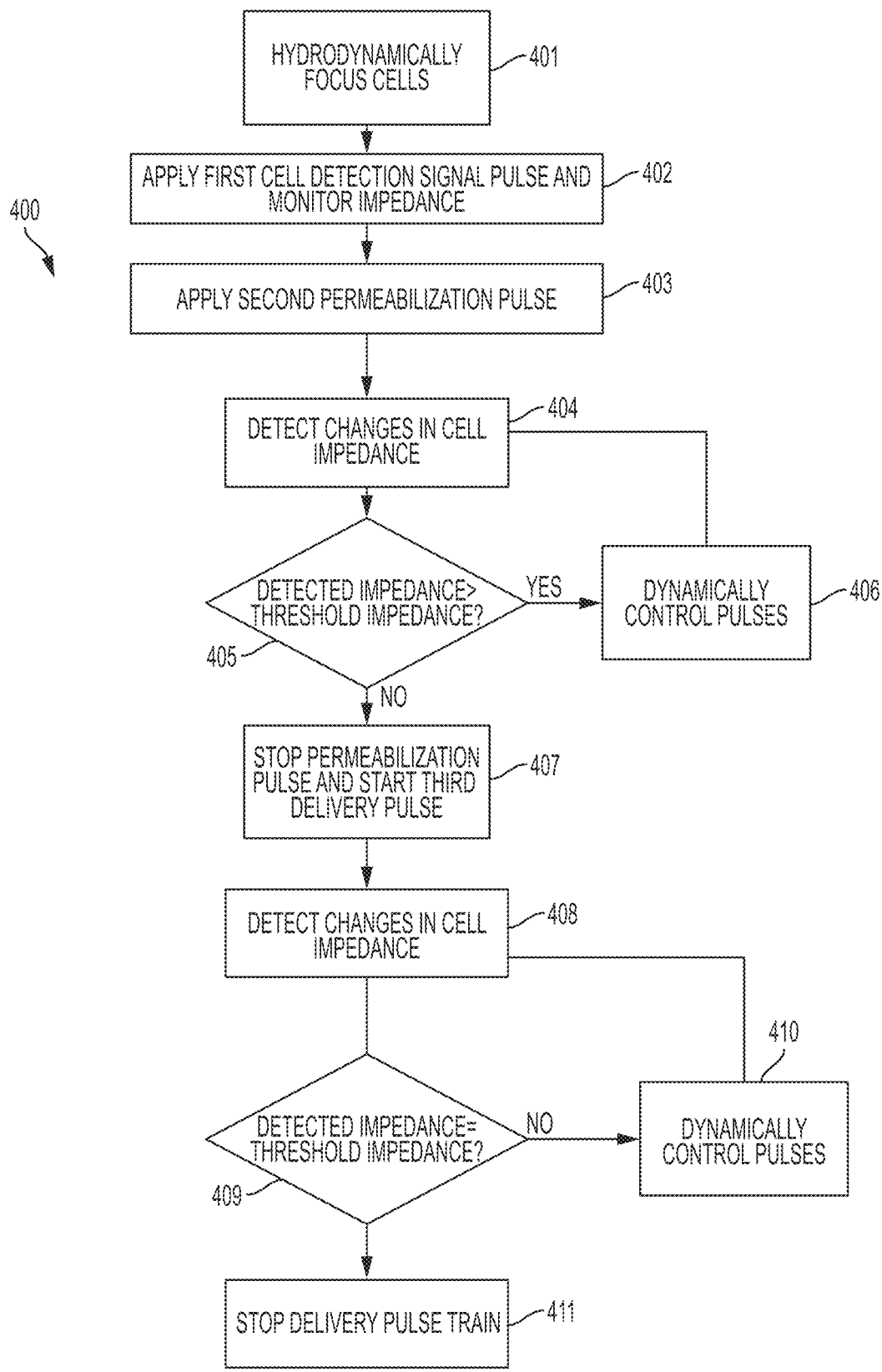
FIG. 4A illustrates a flowchart method of electroporating a cell in a continuous flow, according to an embodiment.

FIG. 4A provides a method 400 for permeabilization of single cells in a continuous flow using the smart electroporation system of FIGS. 3A to 3C. As shown in FIG. 4A, in step 401, cells in a continuous flow system are hydrodynamically focused such that a single cell is introduced into a defined detection area which may trigger the smart electroporation system for signal application and the lock-in amplifier for recording the cell impedance. Concepts relating to hydrodynamic focusing are known to those skilled in the art.

Different cell types may be electroporated using the smart electroporation system, as described herein. Examples may include, without limitation, 3T3 fibroblasts, human dermal fibroblasts (HDFs), and lymphoblastoid cells (LCLs). Cells may be prepared for electroporation using techniques known to those skilled in the art. For example, the 3T3 fibroblasts maybe maintained in complete cell media and cultured to 80% confluency before being harvested for experiments. Prior to electroporation, the cells are trypsinized and resuspended in an electroporation buffer. The electroporation buffer is an iso-osmotic solution of 250 mM sucrose, 10 mM HEPES, and a selected concentration of $MgCl_2$ salt at a pH of 7.4. The amount of $MgCl_2$ added (ranging from 0.4-11.2 mM) determines the final conductivity of that extracellular buffer solution (ranging from 100-2000 μS/cm). The osmolarity of the solution is adjusted to a cell compatible 310 mOsm/kg using an Advanced Osmometer 3D3 (Advanced Instrument, Norwood Mass.). Trypsinized cells are introduced into the middle inlet of a 3-inlet microdevice via syringe pump (Harvard Apparatus, Cambridge, Mass.). The 3-inlet approach hydrodynamically focuses the cells to a width of about 20-25 μm to ensure that the cells enter the center of the operating region of the device in single file.

The systems and methods described in this disclosure may be used to deliver a variety of molecules whose sizes span from hundreds of Daltons to hundreds of thousands of Daltons. Smaller molecules can be delivered efficiently while retaining high levels of cell survival. Larger molecules, on the other hand, may require higher field strengths or longer pulses to drive them into cells, at a cost of greater cell death. By using the "smart" electroporator system of the current disclosure, delivery may be maximized while preserving viability. Examples of molecules that may be delivered into a cell using the systems and methods described herein include, without limitation, small organic compounds, such as drugs and molecular probes, small strands of RNA that are typically used as interfering RNA (siRNA), miRNA, proteins, and plasmid DNA for direct transfection.

In step 402, a first cell detection signal is applied across the detection area and the impedance is monitored. In some embodiments, the first cell detection signal may be an AC detection waveform obtained either from simulation models or known literature. The AC detection waveform may be used to monitor the presence or absence of a cell within the detection area.

In step 403, a second permeabilization signal is applied across the detection area when a biological cell is detected by an increased impedance value over a baseline threshold. In some embodiments, the second permeabilization signal comprises a short-duration, high frequency DC pulse, as described above. The AC detection signal and the DC pulse train waveform are simultaneously applied in the detection area by simple superposition of the two waveforms. In this way, the impedance of the detection area, and cell permeabilization state of the detected cell, can be continuously monitored as the electroporation signal is being applied. In certain embodiments, the AC detection waveform may be separate from the high frequency DC pulse train, and the high frequency DC pulse train may only be applied upon detection of a cell within the detection zone based on impedance changes. In some embodiments, when an permeabilization signal is initiated, detection is temporarily halted until the end of the DC pulse train application. A solid state switch may control the signal paths to prevent generation of electrical artifacts in the Lock-in amplifier sensor from the permeabilization signal.

Figure 6A:
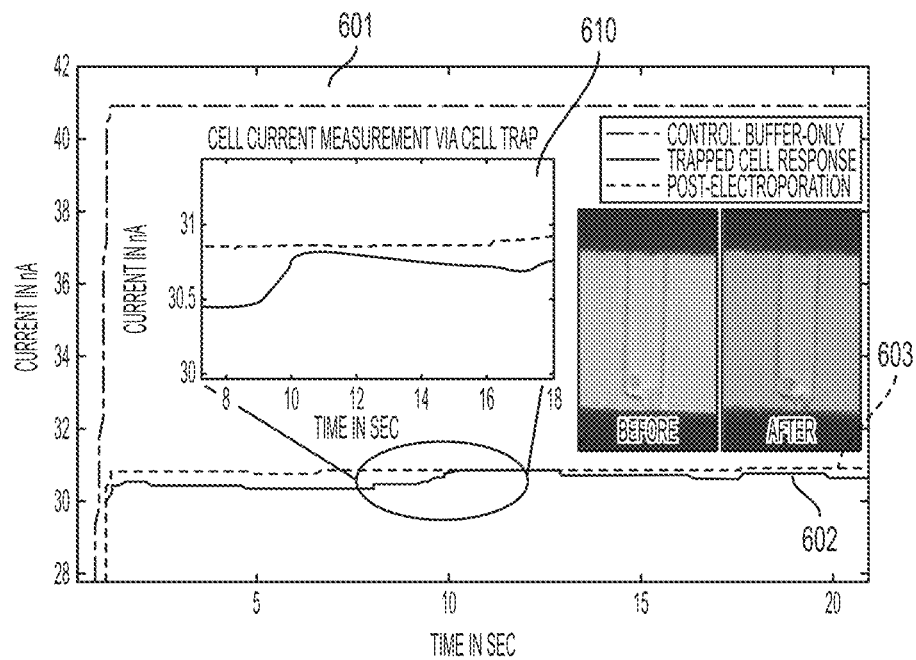
FIG. 6A shows a current magnitude versus time plot illustrating a noticeable increase in cell membrane permeabilization current magnitude under continuous impedance tracking for a trapped cell experiment.
Figure 6B:
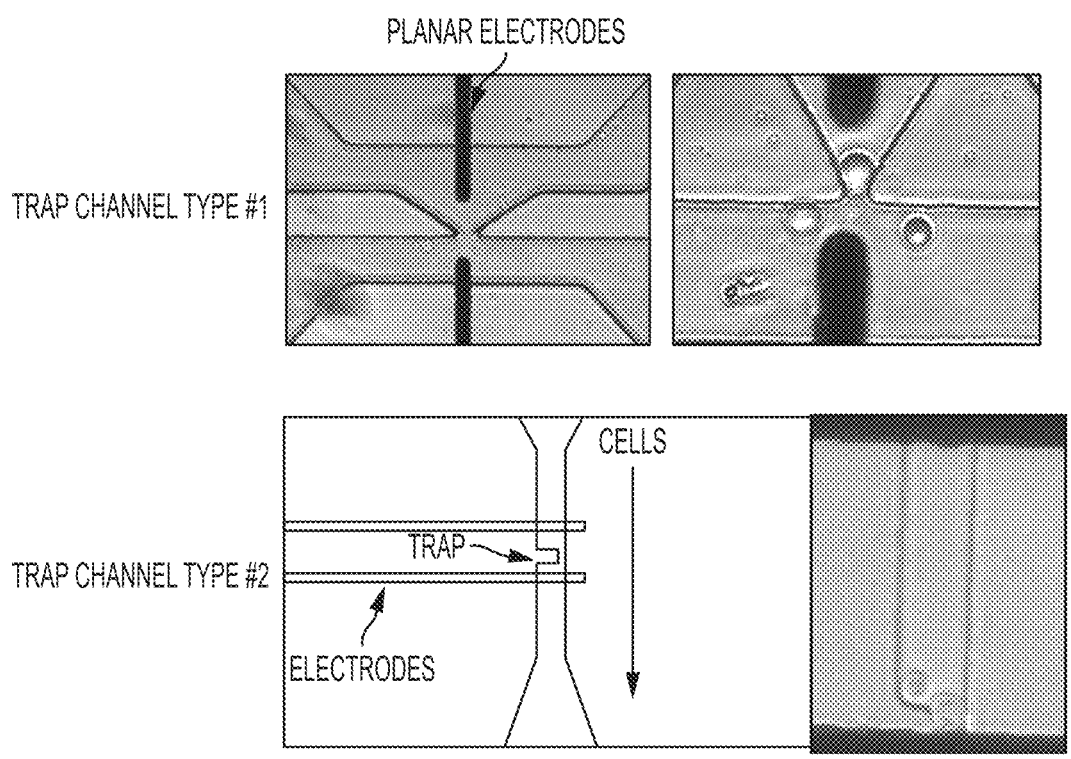
FIG. 6B illustrates microfluidic cell trap channels designed to trap single cell and scan for impedance information.

In an embodiment, the pulse parameters for the AC detection waveform and the high frequency DC pulse train may be chosen based on experimental data received from using the electroporation system on immobilized cells (for a particular cell type). For example, appropriate threshold levels, AC waveform parameters, and DC pulse train parameters may be, cells may be trapped in a microfluidic device with a small cell trap area (<5×5×10 μm) within a pair of electrodes. FIG. 6 shows the lock-in amplifier's impedance detection response to the trapped cells. In an embodiment, a continuous 0.2 Vpp 15 kHz detection signal superimposed over a continuous 2 VDC, 100 KHz, 50% duty cycle permeabilization pulse train may be applied. Line 601 shows the impedance when only solution flows through the channel. Upon introduction of a cell into the trap, the impedance drops dramatically (line 602). A low magnitude (0.2 kV/cm) field continuously may also be applied, so that after a few seconds the cell experienced irreversible electropermeabilization. The increase in current (consistent with the decrease in impedance) remains after the pulse is removed (line 609). The inset 603 shows the channel where the cell was trapped, and the inset 610 shows the current increase during permeabilization. Two separate investigation may then be performed to evaluate the sensitivity and consistency of the detection of impedance changes during electroporation. First, a 100 kHz pulse train of fields of varying strengths and durations, while holding the duty cycle constant, may be applied. The applied field strength may range from 0.1 to 1 kV/cm, and the duration of total applied pulses may range from 10 to 100 ms, to obtain a spectrum of permeabilization outcomes within this parameter space, ranging from no permeabilization to fully and permanently permeabilized. For each combination of field strength and duration, the magnitude of the changes in current may also be recorded. The current change indicating membrane permeabilization may be identified for each condition and examined across conditions for consistency.

Next, after verifying detection of electropermeabilization, the cell trap may be used to calibrate the smart electroporator to detect reversible permeabilization via impedance changes during the application of the pulse train. A series of pulse trains at a field strength of 1 kV/cm (10 VDC, 100 KHz, 50% Duty Cycle) may be applied, but each total pulse duration may be limited to between 1 and 20 ms such that the lower bound of this range may produce reversible permeabilization, whereas the upper bound may produce significant cell death. The above pulse parameters and methods for developing them are provided only for example and may be adjusted without deviating from the principles of the current disclosure.

When the applied pulse train is sub-lethal, the membrane impedance drops during the pulse train, signifying permeabilization of the cell, but recovers once the pulse is terminated and the membrane reseals. However, if the cell is killed by the pulse train, the impedance will not recover. Hence, by varying the total pulse length, a viability threshold impedance change may be determined that is indicative of cell death. The viability threshold impedance change may be used to determine the best pulse parameters for implementing the continuous flow investigation, i.e., a design of AC detection waveform and the high frequency DC pulse train for a particular cell type may be determined. Subsets of the parameter spaces examined in the trapped cells may be applied in the continuous flow smart electroporator and may also be used to evaluate any differences in cell behavior and changes in sensitivity.

In a trapped cell, there is limited buffer surrounding the cell, and the cell contributes a high percentage towards the overall impedance. However, when cells are hydrodynamically focused, a significant amount of fluid may be present on either side of the cell. The changes in cell membrane current may therefore be orders of magnitude smaller than the detection signal of the overall cell from solution current displacement. The greater the relative volume of the cell with respect to the solution buffer within the electrodes, the larger the contribution of the cell (or changes to cell) will be to the current signal. In an embodiment, to reduce the total amount of conductive fluid surrounding the cell, electrically and chemically inert, low surface tension solutions such as halocarbon oils may be used as the sheathing streams in the two lateral inlets to hydrodynamically focus the cell-containing electroporation buffer solution, which is in the central inlet (See FIG. 3C). This can eliminate most of the current noise from the buffer solution by providing a narrow conductive stream in the middle of the channel with a hydrodynamically controllable width. Alternatively and/or additionally, a microchannel design that consists of a gradually narrowed constriction (FIG. 3D) may be employed. This microchannel constriction design serves to increase the cell volume fraction, detection signal to noise ratio, as well as amplify the applied electric field due to concentration of the electric field through the constriction. The length of the microchannel constriction provides the means to increase cell transit time in the detection area, which serves to allow longer time for characterizing detailed electrical information from the cell membrane before, during and after reversible or irreversible electroporation. For example, a 250 μm long constriction with a total cell flow rate of 0.3 μL/min can provide a transit time ranges from 200-400 ms. The width of the constriction is tailored according to the cell size to provide a good fit that allows high electrolyte current displacement and smooth, continuous passage of the single cells through the constriction channel. For example, for NIH 3T3 fibroblast cells with an average diameter of 10-15 μm, a width of 20-25 μm was used to enable both the sheathing fluid and the cell to pass through. The width of the channel is tailorable at the photolithography steps of microchannel fabrication. The depth of the channel may be defined at 10 μm depth to limit the solution volume at the constriction region which is also the detection and pulsing region. The planar electrodes may be placed outside of the channel constriction in order for the amplification of the applied electric field. For a constriction length of 250 μm, electrode distance greater than 260 μm can be used.

Based on the experimental data, in an embodiment, the superpositioned detection/permiabilizing waveforms may be obtained by applying a 1 Vp-p, 20 kHz AC for cell current detection and an permeabilization pulse train with electric field strength determined from the static, cell-trapped experiments (e.g., 1 kV/cm, 10 kHz).

Figure 5A:
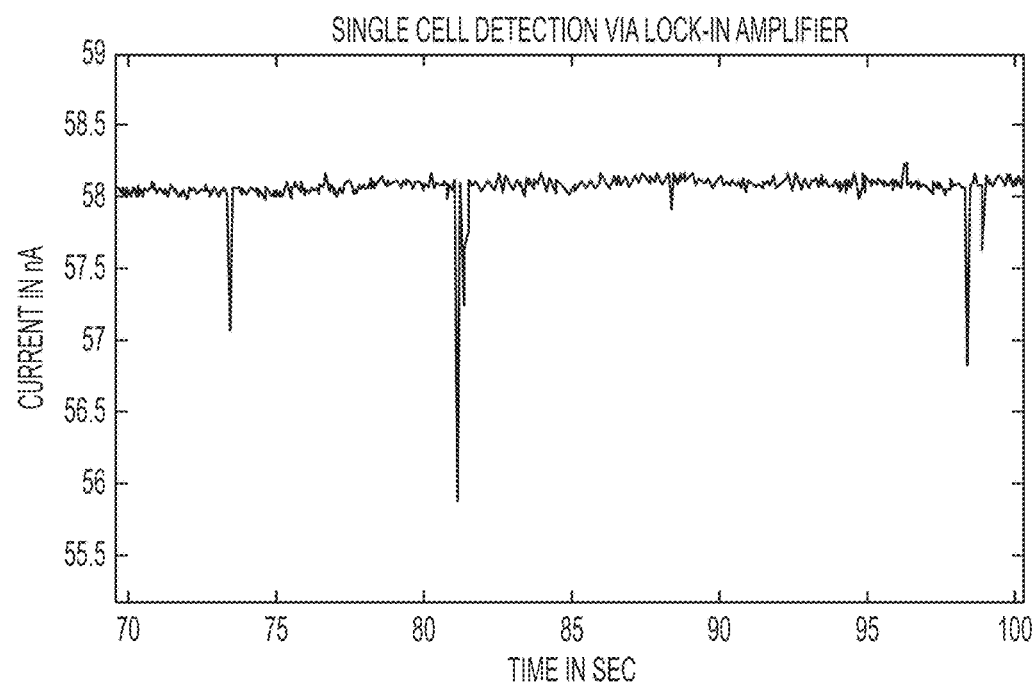
FIGS. 5A and 5B illustrate current magnitude versus time diagrams showing the change in impedance plots for cell detection, according to an embodiment.
Figure 5B:
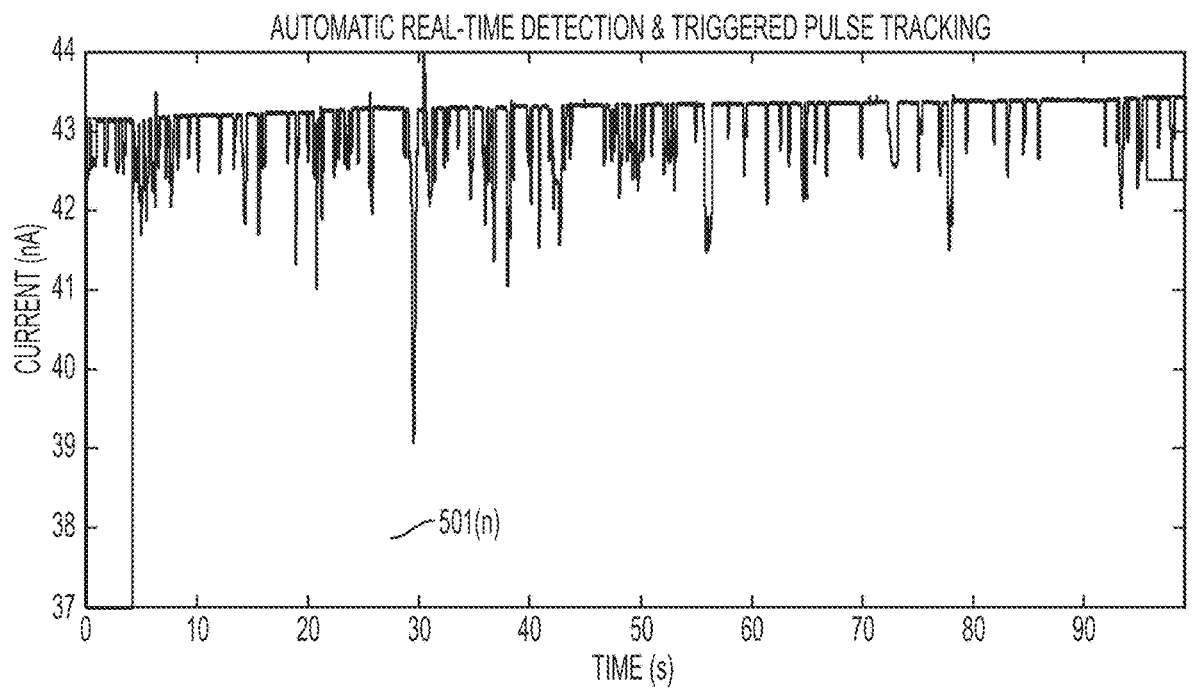

By implementing steps 401 to 403, a prototype signal differential microfluidic channel-based signal detector can be used to detect and enhance cell membrane impedance changes and identify the presence hydrodynamically focused single cells within a microchannel and trigger application of a permeabilization signal to the hydrodynamically focused cell. Experimental data demonstrating this detection and triggered signal is shown in FIGS. 5A and 5B. FIG. 5A shows the single cell detection peaks using the differential signal sensor. The results in FIG. 5A were obtained by applying an AC voltage, 100 mVp-p at 15 kHz to a cell buffer that has a solution conductivity of 100 μS/cm traveling through the microchannel at a flow rate of 0.5 μL/min. The spikes in the signal result from volumetric displacement of the conductive buffer by the cell (hence, displacement of electric current) between the planar electrodes. In an embodiment, electrical measurements for cell detection may also be verified with optical visualization of cells (not shown), via a visualization system integrated with the smart electroporator.

FIG. 5B shows another example of an automatic real-time single cell detection and triggered signal tracking plot illustrating changes in impedance upon detection of each cell in a continuous flow. In the illustrated current-time plot, with the passing of each single cell through the detection area (constriction length), a high 37 dB signal-to-noise ratio was obtained, and each dip 501(n) provides information on the duration, velocity, and impedance magnitude on the cell.

Returning to FIG. 4, in step 404, changes in the cell impedance may be detected by continually monitoring the impedance using a sensing unit. In some embodiments, the sensing unit comprises a lock-in amplifier. A frequency lock-in amplification technique may be implemented to distinguish cell specific signals. The lock-in amplifier acts as a band-pass filter around a reference signal frequency. The noise may be removed by performing a Fourier transform on the input signal at the frequency and phase carried by the reference signal. The reference signal is multiplied by the input signal to generate two output components: one with the frequency equal to the difference between the frequencies of the internal reference and the signal component ($W_R-W_S$) and the other equal to the sum of the two frequencies ($W_R+W_S$). When the frequencies are equal ($W_R=W_S$), the first component produces a DC signal and the second will have twice the reference frequency (2WR). A low-pass filter rejects everything but the DC component. The signal is separately multiplied by independent reference sine and cosine waves to extract the phase information required to calculate the amplitude of the final signal.

To determine the optimal sensing frequency for the lock-in amplifier, an impedance analyzer may be used. The impedance analyzer may determine the cell impedance as a function of frequency both prior to and post electroporation. By characterizing the impedance before and after electroporation, the optimal frequency for the lock-in amplifier to sense the largest variation in impedance due to membrane breakdown may be determined. The detection frequency may then be set to the expected frequency range to lock onto the cell membrane impedance change in a channel to optimize the detection and quantification of the increase in membrane conductance resulting from electroporation-induced cell membrane permeabilization.

For a superimposed detection/permeabilization pulse, two distinct optimal frequencies may be used to distinguish the cell detection impedance change from the permeabilization detection impedance change and the applied frequency range may be rapidly modulated from the optimal frequency for detecting cells in the detection area to the optimal frequency for detecting permeabilization, upon sensing a cell. For example, a 90V N-channel fast switching POWERTRENCH MOSFET (FDS6298, Fairchild Semiconductor, Huntsville, Ala.) module with the function generator may be configured to switch between the two predetermined frequencies at nanosecond speed (from 20 kHz for cell detection to MHz range for membrane impedance change) once a cell signal is detected.

While the current disclosure utilizes a lock-in amplifier for monitoring cell impedance changes, other now or hereafter known methods for monitoring impedance changes are within the scope of this disclosure.

In step 405, the detected impedance value may be compared to a permeabilization threshold impedance, where the threshold impedance is indicative of a desired level of permeabilization of the cell. The threshold impedance value may be selected to ensure cell viability (i.e., sub-lethal permeabilization). The threshold impedance may be calculated using the trapped cell experimental data for a particular cell, or using a mathematical model. If the detected impedance value is found to be greater than the threshold impedance, the pulse parameters of the DC permeabilization signal of step 403 may be dynamically controlled (406) using a control signal, and the steps may be repeated till the desired threshold impedance is detected. A control signal may be generated to alter signal parameters, using the trapped cell experimental data for a particular cell (as discussed above), or using a mathematical model. At the desired threshold impedance, the cell may be permeabilized to desired level, i.e., sub-lethal permeabilization. The desired level of permeabilization may correspond to maximal membrane permeabilization without cell death. With a DC pulse train, there are several interrelated parameters that can potentially affect the delivery efficiency during electroporation, which may be altered to achieve the desired permeabilization: electric field amplitude, pulse duration, pulse train frequency, duty cycle and number of cycles. For example, a 50 kHz pulse train has a 20 µs pulse period, and with a 50% duty cycle, each pulse is 10 µs long. To obtain a 10 ms total pulse application, 1000 cycles are applied for 20 ms at 50 kHz frequency. The duty cycle controls the amount of rest period following each pulse. Any of the above parameters may be altered to achieve the desired premebilization level without causing electrolysis of the cell. For example, in an embodiment, the duty cycle can be tuned to increase the pulse width improving delivery time at the cost of electrolysis with the pulse train becoming more like a single DC pulse, or decreased to reduce delivery time while increasing the number of pulses to minimize electrolysis.

In step 407, detection of sublethal permeabilization in step 405, the permeabilization signal may be stopped and a discrete delivery signal may be introduced in the detection area. The delivery signal may be a low strength electric field to induce influx of charged species. In an embodiment, the delivery signal may comprise a DC pulse train that may range from of 0.1-1 kV/cm in magnitude and 10-100 ms in duration. The AC detection signal and the delivery DC pulse train waveform may be simultaneously applied in the detection area by simple superposition of the two waveforms. In this way, the impedance of the detection area, and cell permeabilization state of the detected cell, can be continuously monitored as the delivery signal is being applied.

The delivery pulse train may be predesigned based on the pulse characteristics of the detection and permeabilization signals, cell type, cell size, buffer characteristics, and other properties as discussed above with respect to the permeabilization signal. The delivery pulse train may also be dynamically controlled 410 using a feedback control that continuously monitors the impedance changes (408) and compares (409) it to the permeabilization threshold impedance (corresponding to the sublethal permeabilization), in order to maintain the field strength in a regime where pores remain open to allow molecular delivery without reaching excessive changes in impedance indicative of cell death. As such, the second pulse train characteristics can be dynamically altered to maximize delivery potential. For example, impedance characteristics may be monitored to detect pore closure, stabilization, and permanence based on trapped-cell experiments, mathematical models, and/or previously performed continuous flow measurements in the smart electroporator system.

When the viability threshold for over-exposure is approached even as the field is lowered, or when the impedance value returns to the baseline threshold indicating that the cell has flowed through the detection area, the field will be discontinued 411. In an embodiment, the impedance changes may be monitored using the intracellular current reading sampled at 100 kHz by the lock-in amplifier, and iteratively checked against the predicted permeabilization state.

Figure 4B:
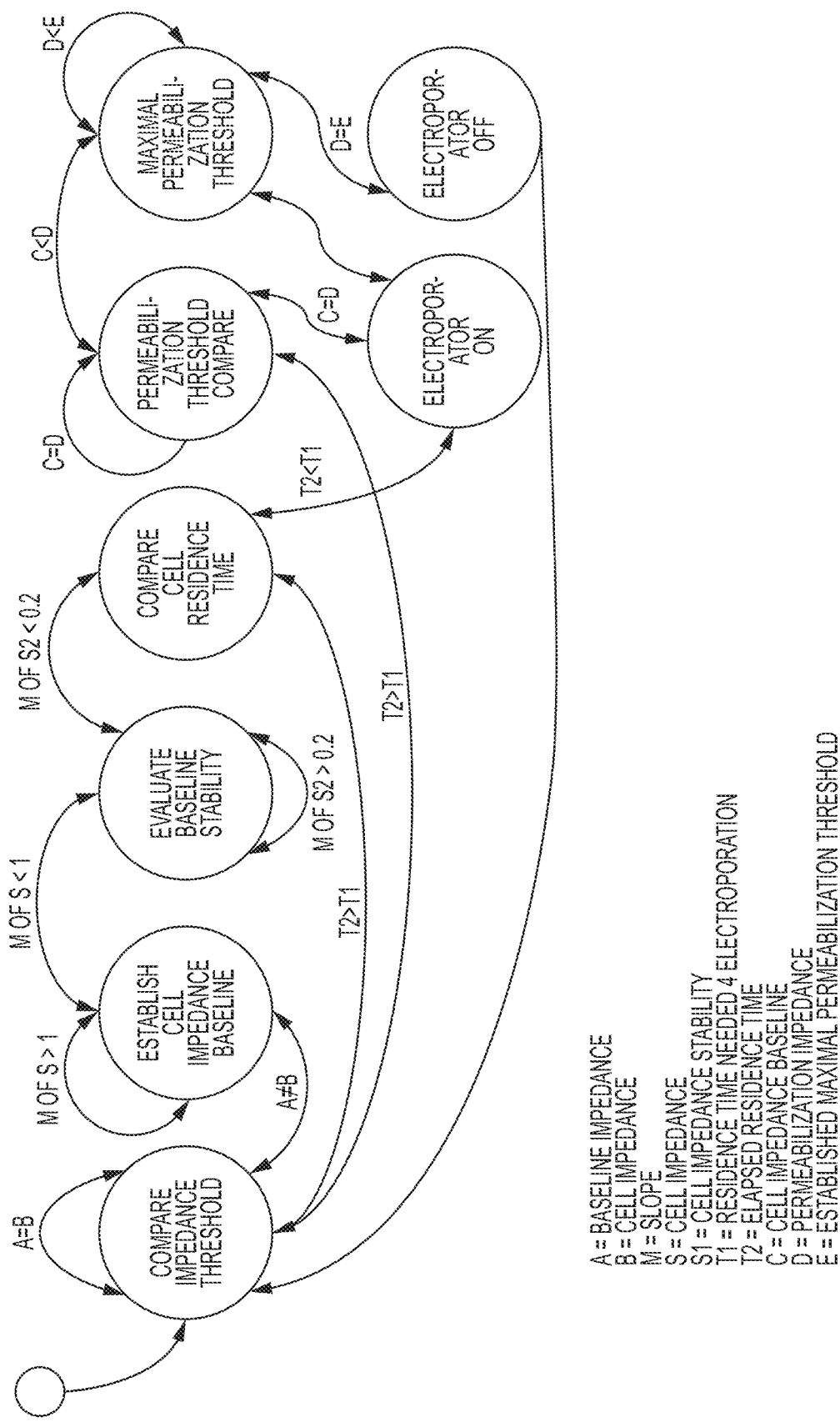
FIG. 4B shows a state diagram illustrating the operation of the automatic electroporation control algorithm for performing the steps of FIG. 4A, according to an embodiment.

FIG. 4B illustrates a state diagram of the algorithm for performing at least some of the steps of FIG. 4A.

Figure 8A:
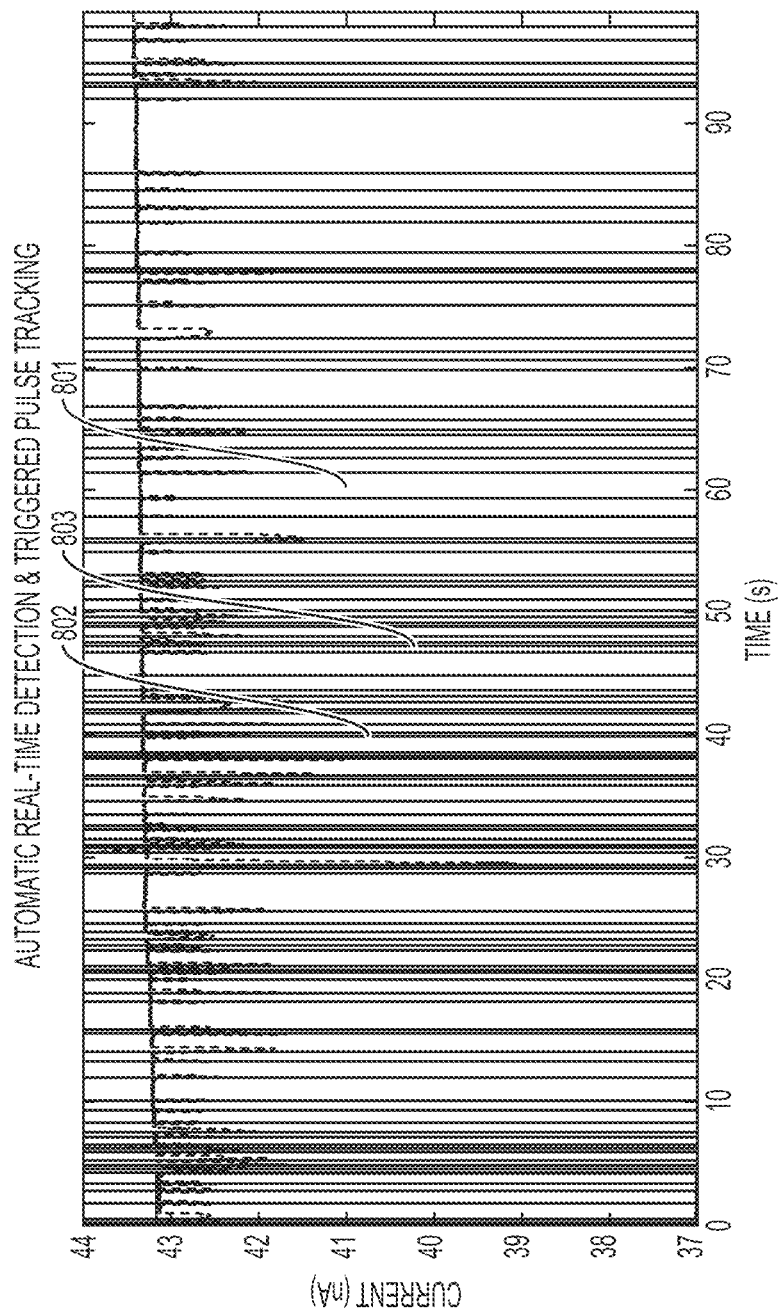
FIGS. 8A-8D illustrate current versus time diagrams showing the change in impedance plots for cell detection, permeabilization and delivery, according to an embodiment.

Exemplary data utilizing the systems and methods of the present disclosure is shown in FIGS. 8A-8D. FIGS. 8A-8D illustrate overall cell current displacement and cell membrane impedance change plots and the corresponding pulses. FIG. 8A illustrates automatic real-time single cell detection and triggered pulse tracking plot showing that the above system and method detects and electroporates each passing single cell with a high accuracy. Each vertical line 803 represents an automated application of a 5-ms pulse train with predefined pulsing parameters, in this case, a 0.6 kV/cm field strength DC pulse train was applied. Each dip 801 on the impedance curve 802 represents the passing of a single cell, and illustrates an automatic electroporation accuracy of 93.7% with an accuracy of 1.3 cells/s.

Figure 8B:
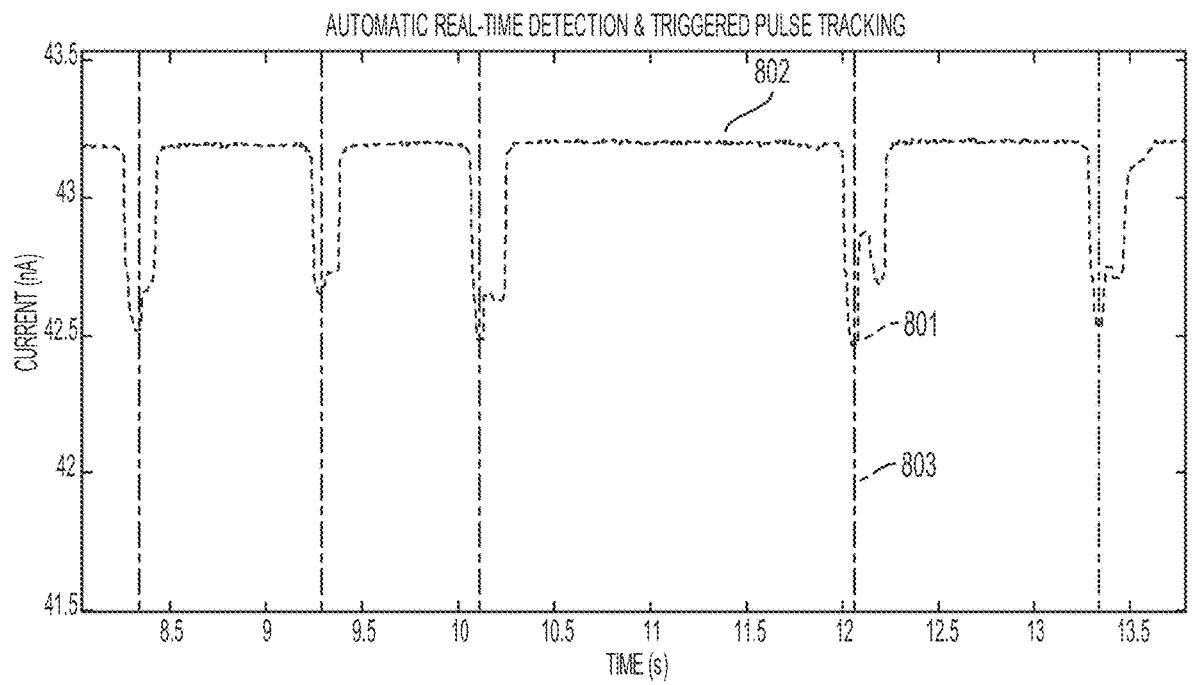

FIG. 8B is a zoomed in illustration of five cells from FIG. 8A in the 8 s-14 s time slot, and distinctive information regarding the cell state before and after permeabilization signal application is shown. For a current-time plot, each sharp drop-off in current signal indicates the presence of a single cell within the pulsing zone, and the return of this dip into its original baseline indicates the departure of the cell from the pulsing zone. For these five cells, an average transit time of ~900 ms is observed, along with a current rise following the signal application.

Figure 8C:
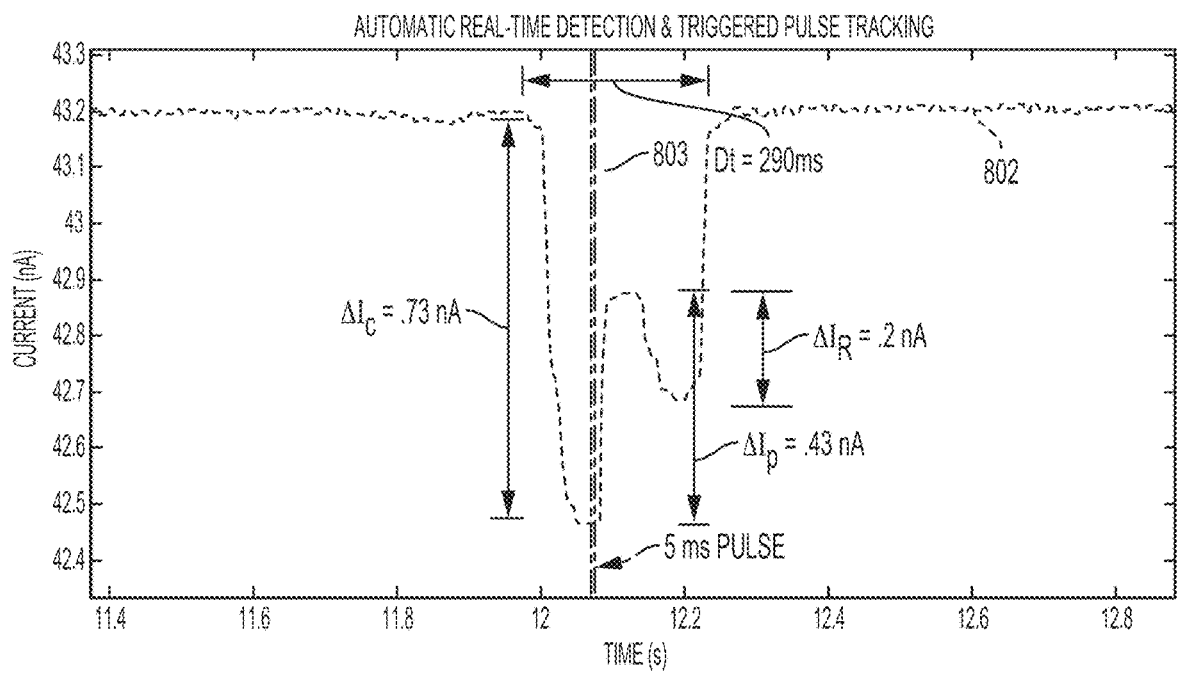

FIG. 8C illustrates a zoomed in plot of a single cell from FIG. 8B. $\Delta I_c$ denotes the current displacement signal which for this case is 0.72 nA, and $\Delta I_p$ denotes the change in permeabilization signal which varies depending on the magnitude and duration of pulse applied to the cell. $\Delta I_r$ denotes the membrane resealing current for which the membrane may be resealed for a cell receiving non-lethal pulse.

Figure 8D:
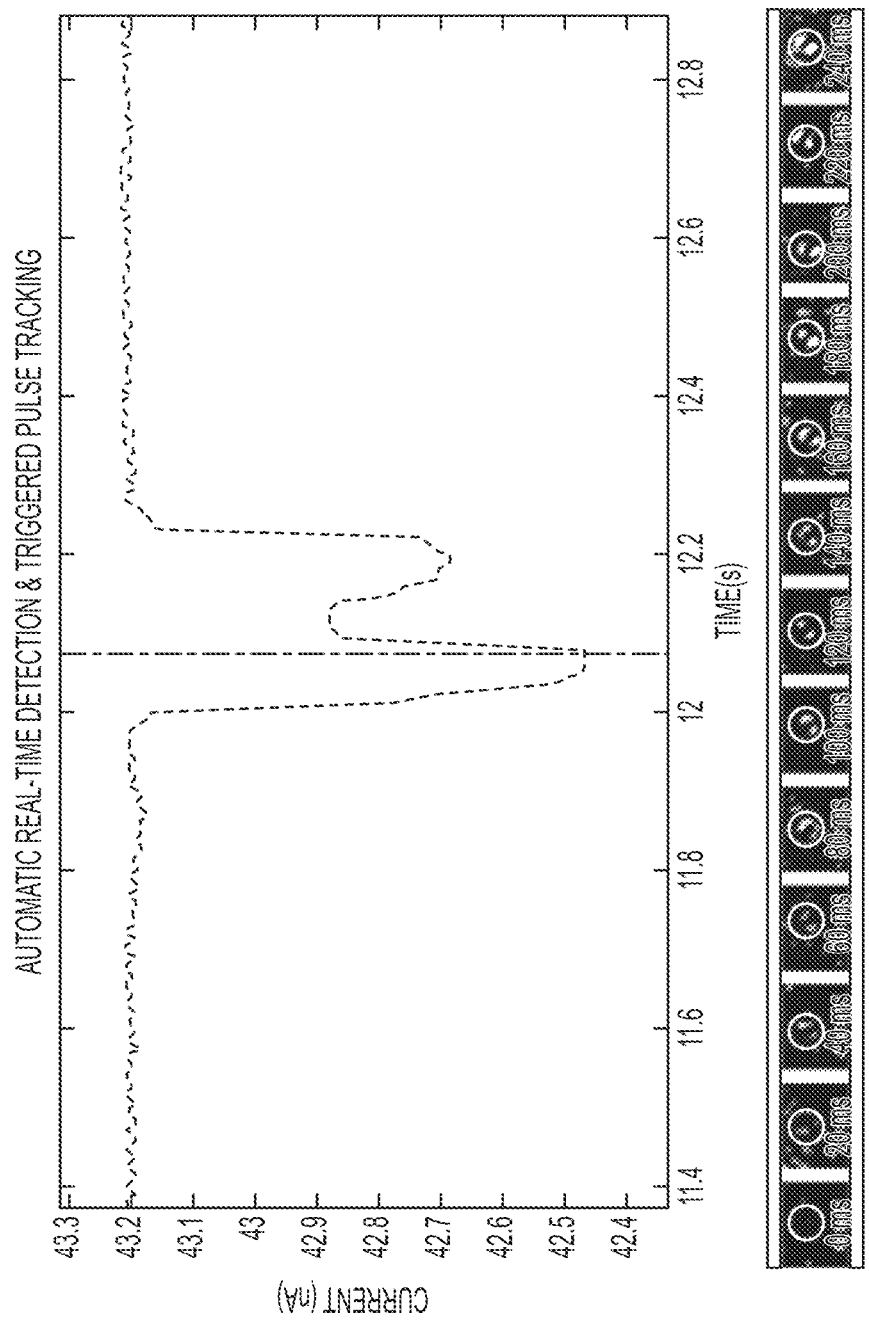

FIG. 8D illustrates temporal tracking of a nucleic acid binding dye (Propidium Iodide) being delivered into the flowing single cell (bottom strip). At the 20 ms time mark, a 5 ms pulse train at 0.6 kV/cm field amplitude was applied, and the rate of fluorescent intensity was continuously tracked to show steady increase due to opening of membrane pores, and a slowdown in intensity rate after passing the observed permeabilization peak, which we believe indicates the membrane pores resealing.

Figure 9:
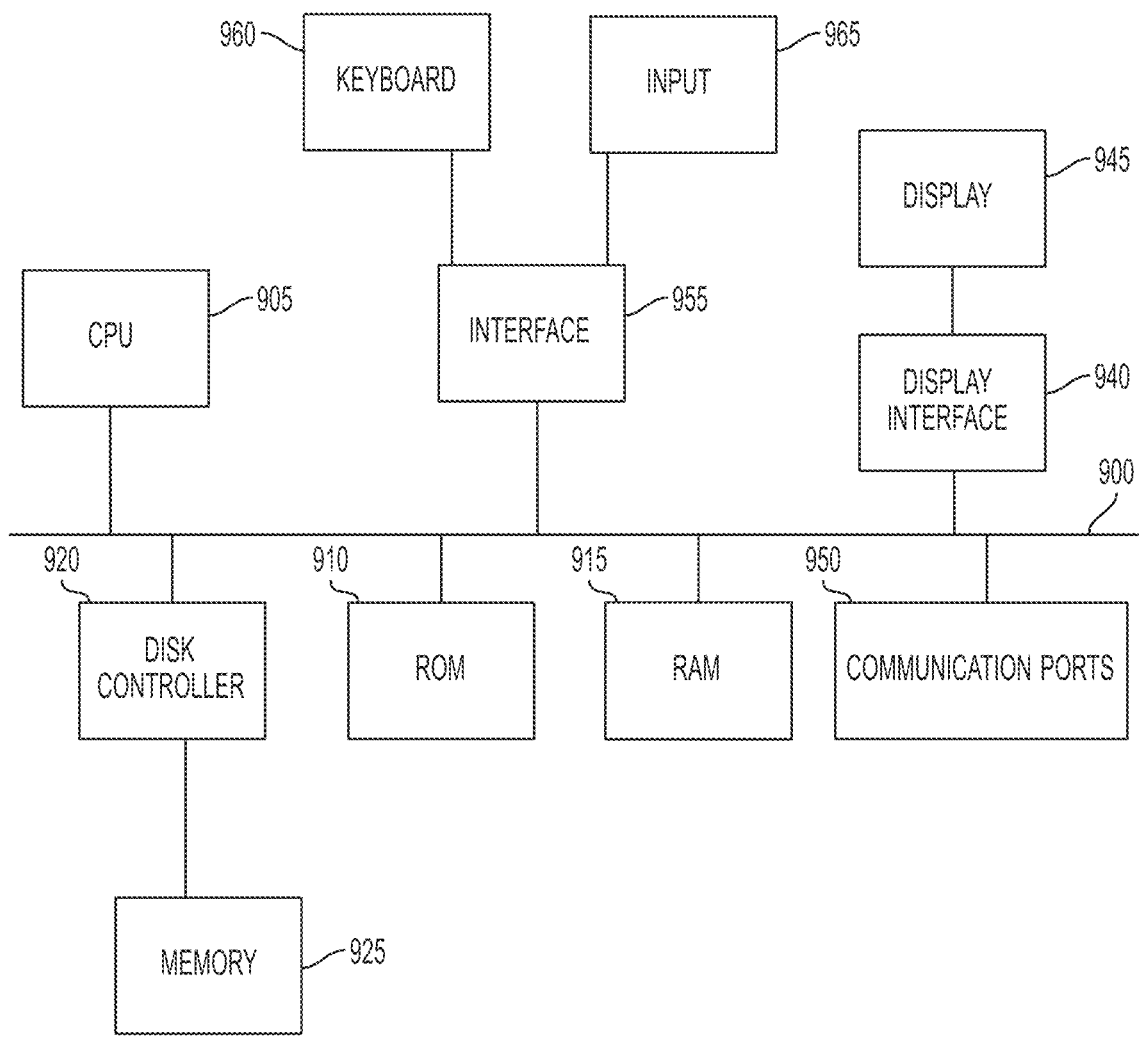
FIG. 9 is a block diagram that is useful for understanding exemplary computer hardware which is capable of implementing the methods described herein.

FIG. 9 depicts an example of internal hardware that may be used to contain or implement the various computer processes and systems as discussed above. For example, the smart electroporation discussed above may include hardware such as that illustrated in FIG. 9. An electrical bus 900 serves as an information highway interconnecting the other illustrated components of the hardware. CPU 905 is a central processing unit of the system, performing calculations and logic operations required to execute a program. CPU 905, alone or in conjunction with one or more of the other elements, is a processing device, computing device or processor as such terms are used within this disclosure. A CPU or "processor" is a component of an electronic device that executes programming instructions. The term "processor" may refer to either a single processor or to multiple processors that together implement various steps of a process. Unless the context specifically states that a single processor is required or that multiple processors are required, the term "processor" includes both the singular and plural embodiments. Read only memory (ROM) 910 and random access memory (RAM) 915 constitute examples of memory devices. The term "memory device" and similar terms include single device embodiments, multiple devices that together store programming or data, or individual sectors of such devices.

A controller 920 interfaces with one or more optional memory devices 925 that service as date storage facilities to the system bus 900. These memory devices 925 may include, for example, an external or internal disk drive, a hard drive, flash memory, a USB drive or another type of device that serves as a data storage facility. As indicated previously, these various drives and controllers are optional devices. Additionally, the memory devices 925 may be configured to include individual files for storing any software modules or instructions, auxiliary data, incident data, common files for storing groups of contingency tables and/or regression models, or one or more databases for storing the information as discussed above.

Program instructions, software or interactive modules for performing any of the functional steps associated with the processes as described above may be stored in the ROM 910 and/or the RAM 915. Optionally, the program instructions may be stored on a non-transitory, computer readable medium such as a compact disk, a digital disk, flash memory, a memory card, a USB drive, an optical disc storage medium, and/or other recording medium.

An optional display interface 940 may permit information from the bus 900 to be displayed on the display 945 in audio, visual, graphic or alphanumeric format. Communication with external devices may occur using various communication ports 950. A communication port 950 may be attached to a communications network, such as the Internet, a local area network or a cellular telephone data network.

The hardware may also include an interface 955 which allows for receipt of data from input devices such as an imaging sensor 960 of a scanner or other input device 965 such as a keyboard, a mouse, a joystick, a touchscreen, a remote control, a pointing device, a video input device and/or an audio input device.

EXAMPLES

The present invention is described more fully by way of the following non-limiting examples. Modifications of these examples will be apparent to those skilled in the art.

Example 1

To determine the optimal channel geometry and sensing frequency required to detect cell-membrane permeabilization, a cell/electrolyte equivalent circuit was constructed to model the single-cell electrical-impedance response in a microfabricated flow cytometer. This circuit model was adapted from previous models to account for the dramatic increase in cell-membrane conductance during electroporation. The model allows determination of the impedance of a cell suspended in buffer between a pair of electrodes as shown in FIG. 7C, where $C_{DL}$ is the double layer capacitance. $R_m$ and $C_m$ are the resistance and capacitance of the extracellular media, respectively. $C_{mem}$ is the capacitance of the cell membrane and $R_i$ is the cell's internal resistance. To reflect the overall impedance change as a result of cell-membrane permeabilization by electroporation, a variable $R_{mem}$ was implemented in parallel to $C_{mem}$. The resultant overall impedance equation for describing a membrane permeabilized cell including double layer effect is shown in Equation 1.

$$|Z| = \frac{1}{j\omega C_{DL}} + \frac{\left(R_m\left(1 + R_i\left(j\omega C_{mem} + \frac{1}{R_{mem}}\right)\right)\right)}{\left(R_m\left(j\omega C_{mem} + \frac{1}{R_{mem}}\right) + \left(1 + R_i\left(j\omega C_{mem} + \frac{1}{R_{mem}}\right)\right)\right)(1 + j\omega R_m C_m)} \quad (1)$$

|Z| is the impedance magnitude of the single cell, w is the angular frequency, and the formula for calculating the values of the individual electrical components, except for $R_{mem}$, may be known to those skilled in the art. $R_{mem}$ is based on the resistance of a typical patch of membrane $R_M$=10000 $\Omega/cm^2$, and assuming a spherical cell with radius r can be calculated as follows:

$$R_{mem} = \frac{R_M}{4\pi r^2}.$$

Electro-permeabilized cell membrane resistance $R_{porated\_mem}$ is conservatively approximated based model, assuming only 0.1% of the cell membrane is porated.

$$G_{mem} = 0.001 \sigma_m \left(\frac{\pi r^2}{2d}\right)$$

where d is the membrane thickness of 5 nm and $\sigma_m$ is the buffer conductivity at 100 µS/cm.

Figure 7A:
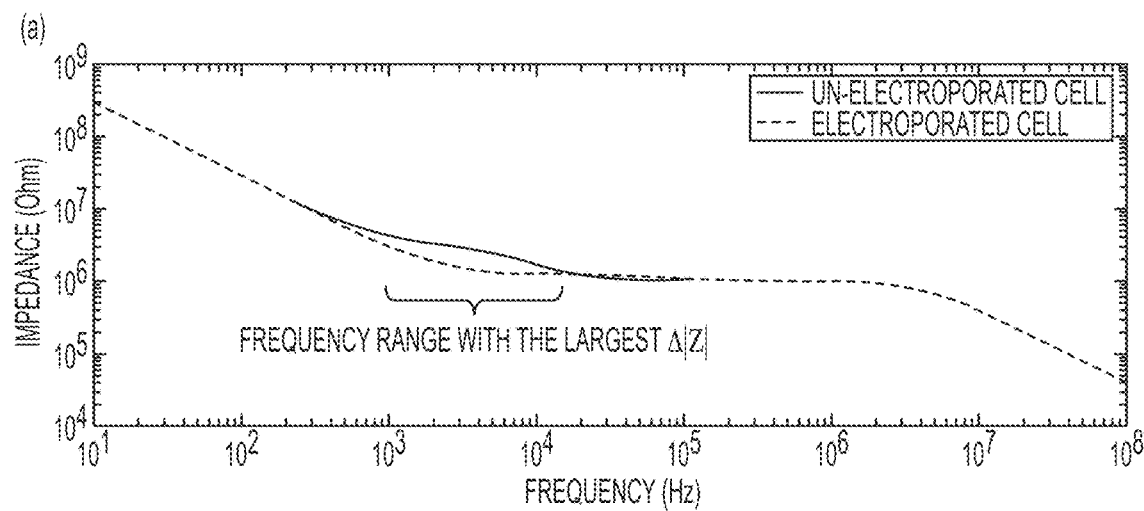
FIGS. 7A and 7B represent the threshold impedance modeling and corresponding experimental data, respectively, according to an embodiment.
Figure 7B:
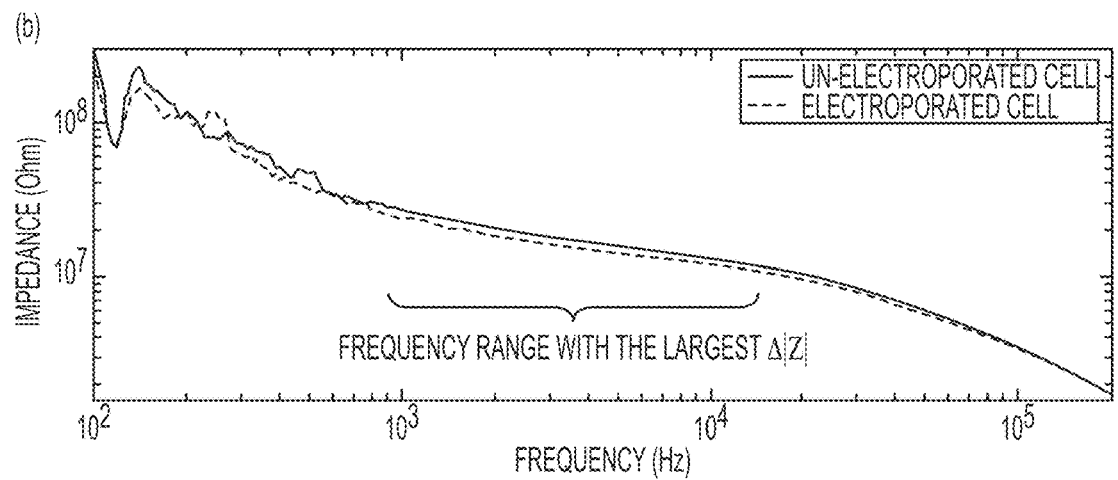
Figure 7C:
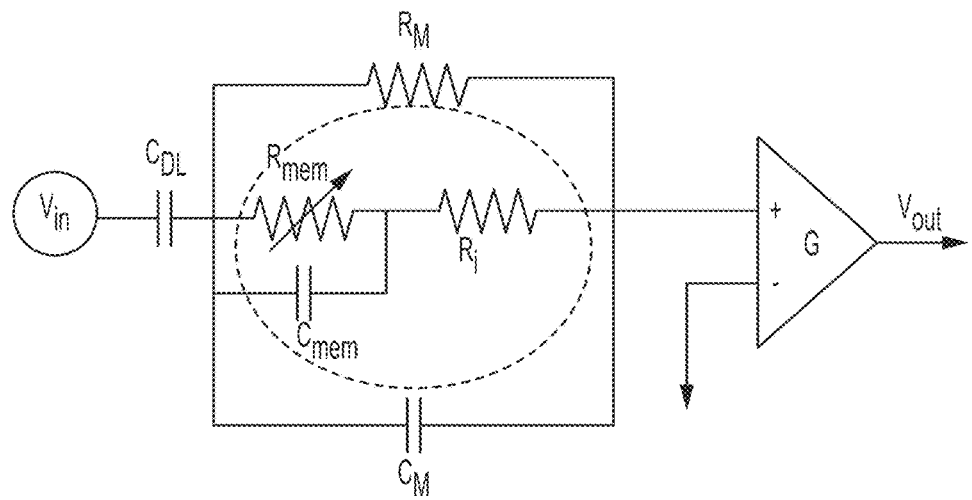
FIG. 7C represents a model cell/electrolyte equivalent circuit, according to an embodiment.

The impedance magnitude for an untreated cell was plotted and overlapped with the electroporated cell (FIG. 7A). Change in impedance Δ|Z| as a result of varying $R_{mem}$ from an intact (high $R_{mem}$) to permeabilized cell membrane state (low $R_{mem}$) falls in a frequency region between 1 and 10 kHz. The corresponding experimental data (FIG. 7B) in which a frequency sweep (100 Hz to 100 kHz) was performed on an individual cell suspended in 100 µS/cm buffer before and after electroporation demonstrated a comparable impedance change in the frequency range predicted by the model.

To determine factors influencing Δ|Z| following electroporation, the cell volume fraction and extracellular buffer conductivity were systematically varied as a function of sweeping frequency. It was determined that the largest Δ|Z| following electroporation is dictated by both cell volume fraction ($V_{cell}/V_{channel}$) and buffer conductivity at a lower frequency spectrum. By using a micro-constriction channel to provide a cell-volume-fraction of 5% and extracellular buffer conductivity at 100 µS/cm, the greatest change in cell membrane permeabilization following electroporation can be found using frequency ranges from 1 to 10 kHz.

Example 2

Methods and Materials

The device consists of a pair of planar electrodes on a glass substrate and a polydimethylsiloxane (PDMS) microchannel fabricated via soft lithography. The silicon master mold with the device feature was fabricated using standard photolithographic procedures. The device main channel is 1 mm long, 150 µm wide, and 10 µm deep, incorporating a constriction with a dimension of 250 µm (L)×25 µm (W)×10 µm (D). Briefly, a 10:1 mixture of PDMS polymer and hardening agent was poured onto the mold to create a negative replica and allowed to cure at 65° C. overnight. Holes were punched in the PDMS to create access to the inlet channel (0.5 mm in diameter) and to the outlet reservoir (1.5 mm in diameter). Titanium/Platinum (Ti/Pt) planar electrodes were fabricated via a metal 'lift-off' process. Traces for the electrodes were patterned lithographically on glass substrates and recesses were etched with 10:1 buffered hydrofluoric acid for 1 minute to a depth of ~2000 Å. The metals were deposited via physical vapor deposition (KJL PVD75, Kurt J. Lesker Co.) followed by dissolution of the photoresist in acetone leaving behind the electrode traces. The resultant Ti/Pt electrodes were 50 µm in width, with a center-to-center spacing of 300 µm. This distance allowed for sufficient cell transit time for electrical and optical analysis without compromising SNR quality. The surfaces of the PDMS and the glass substrate with patterned electrodes were treated under oxygen plasma at 100 W power, 250 sccm $O_2$ at 700 mTorr for 60 s (PX-250, March Instruments). The activated substrates were aligned using a stereo-microscope (SZ61 Binocular Stereo Zoom, Olympus) and irreversibly bonded. Copper wires were bonded to the planar electrode pads via conductive epoxy.

Prior to each experiment, the microchannel was pre-treated with a 10% bovine serum albumin (BSA) solution at room temperature for one hour to prevent unwanted cell adhesion to the channel surfaces. The microchannel was then drained, and excess BSA solution was removed from the outlet reservoir and replaced with 10 µL of Dulbecco's modified Eagle's medium (DMEM) media. NIH 3T3 mouse fibroblasts were cultured in DMEM supplemented with 10% v/v fetal bovine serum, 1% v/v penicillin-streptomycin and 1% l-glutamine (Sigma-Aldrich, St. Louis, Mo.). Cells were cultured to ~70% confluency before being harvested for experiments. The harvested cells were suspended in an iso-osmotic electroporation buffer consisting of 250 mM sucrose, 10 mM HEPES, and 0.4 mM of $M_gCl_2$ salt to provide a conductivity of 100 µS/cm. A precision microfluidic syringe pump (PicoPlus, Harvard Apparatus) was used to perfuse the cells at a flow rate of 0.1 µL/min, resulting in an average cell transit time of 250 ms across the microchannel constriction. Once a stable flow of single cell was established, the electroporation system was initiated upon user command Five electric fields (0.44, 0.58, 0.70, 0.87, 1.05 kV/cm, as measured at the cell) were investigated at five pulse durations each (0.2, 0.8, 1.0, 3.0, 5.0 ms) to impose different degrees of cell-membrane permeabilization. Two cell assays were carried out to validate the electroporation system. During the first assay, propidium iodide (PI) (P3566, Life Technologies), a cell-membrane impermeant dye which fluoresces upon binding to cytosolic nucleic acids, was added to the electroporation buffer at 100 µM total concentration to optically signal membrane permeabilization. The electrical signal from a lock-in amplifier (HF2LI Lock-in Amplifier, Zurich Instruments) and the fluorescence intensity of PI delivery were recorded for each individual cell. In the second assay, single cells underwent the same electroporation treatments without PI addition. Following each prescribed pulse treatment, approximately 2000 cells were collected over 20 minutes from the outlet reservoir for viability assessment. The collected cells were washed in 1× PBS buffer via centrifugation at 2000 RPM for 2 minutes, then incubated with 2 µM of 7-Aminoactinomycin D (7AAD) (7AAD, ThermoFisher Scientific) on ice for 20 minutes to allow cell-viability staining. The cells were then washed again in 1× PBS buffer prior to be imaged under a fluorescence microscope. A semi-automated cell-scanning-and-processing algorithm written in MATLAB (MATLAB R2012b, Mathworks) was used to process the fluorescence intensity of the collected cells.

The lock-in amplifier was used to dynamically extract the signal and apply the electroporation pulse. A custom-built LabVIEW control algorithm was loaded onto the lock-in amplifier's embedded system for real-time processing. One device electrode was connected with the lock-in amplifier's waveform generator output via Lead I to deliver a sensing excitation signal of 1 $V_{p-p}$, while the other electrode was connected to a low-noise current preamplifier input (HF2CA Current Preamplifier, Zurich Instruments) via Lead II prior to passing the signal to the lock-in amplifier sensor. A frequency of 1.224 kHz was chosen to provide both optimal cell detection via the derivative-based peak-detection algorithm and the most sensitive cell-membrane permeabilization detection with the highest SNR. When a cell is detected within the electroporation zone, an electroporation pulse is instantly delivered by a function generator (33220A Waveform Generator, Agilent) through Lead I to the monitoring oscilloscope via Lead III. The pulse was programmed in the function generator and fed to a high-voltage amplifier (Model 2350, TEGAM) to supply electric field pulses ranging from 0.44 to 1.05 kV/cm with a duration between 0.2 and 5.0 ms. A CMOS switch (DF419DJ+ Analog Switch, Maxim Integrated) synchronized with the function generator was added in series with the lock-in amplifier's preamplifier input to prevent measurement artifacts from the electroporation pulse. The pulse trigger signal was also split to the external trigger input of a microscope mounted CMOS camera (PowerView 1.4MP, TSI) to simultaneously capture images of PI entry into cells following each pulse.

Results

Automated Cell Detection & Electroporation

Automated detection of single cells and immediate pulse application to each cell with a throughput of 1.3 cells/sec was obtained. Cell transit across the constriction length yields a stable baseline current due to the constant volume displacement in the channel. An estimated cell-transit time of 250 ms provided an ample temporal window for electroporation and post-pulse impedance measurement. In this representative plot, the vertical red line depicts the application of a prescribed electroporation pulse, in this case a 1.05 kV/cm electric field for 5.0 ms. A sharp rise in current is immediately observed after administering the pulse. This jump in current results from the increase in cell-membrane conductance and is characteristic of the formation of pores as a result of electroporation-induced cell-membrane permeabilization. As the cell departs from the channel constriction, the electrical signal returns to the buffer-solution baseline. This process repeats for each cell traversing through the electroporation zone. A signal to noise ratio (SNR) of 37 dB was measured for the single-cell detection. The system maintained a 97% accuracy in detecting and pulsing each cell as compared to optical observations. Error was primarily attributed to the occasional tailgating of multiple cells, leading to multiple-pulse application to each cell in transit.

Cell Membrane Permeabilization Analysis

Figure 10:
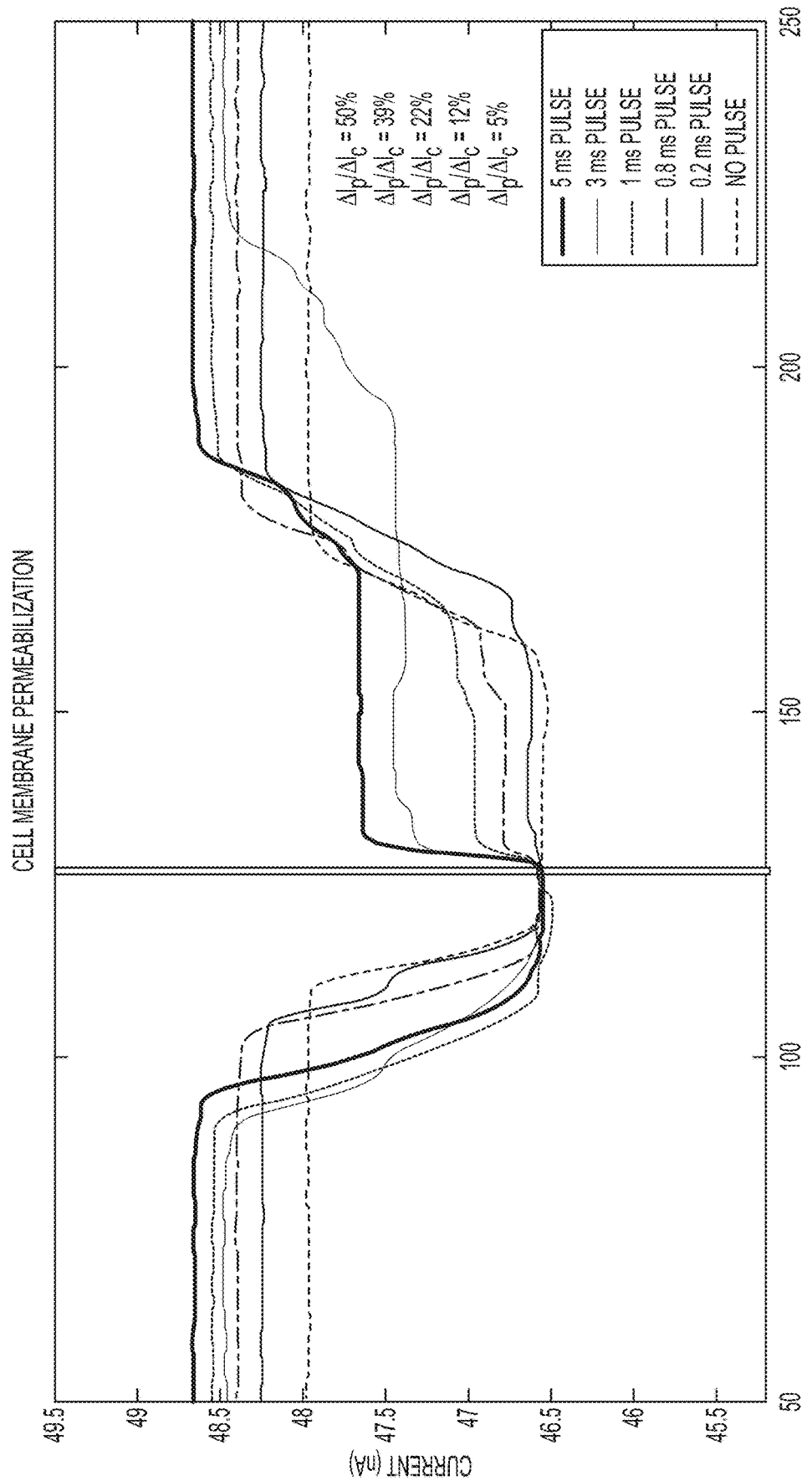
FIG. 10 shows the characterization of the cell membrane response as a function of duration, according to an embodiment.
Figure 11:
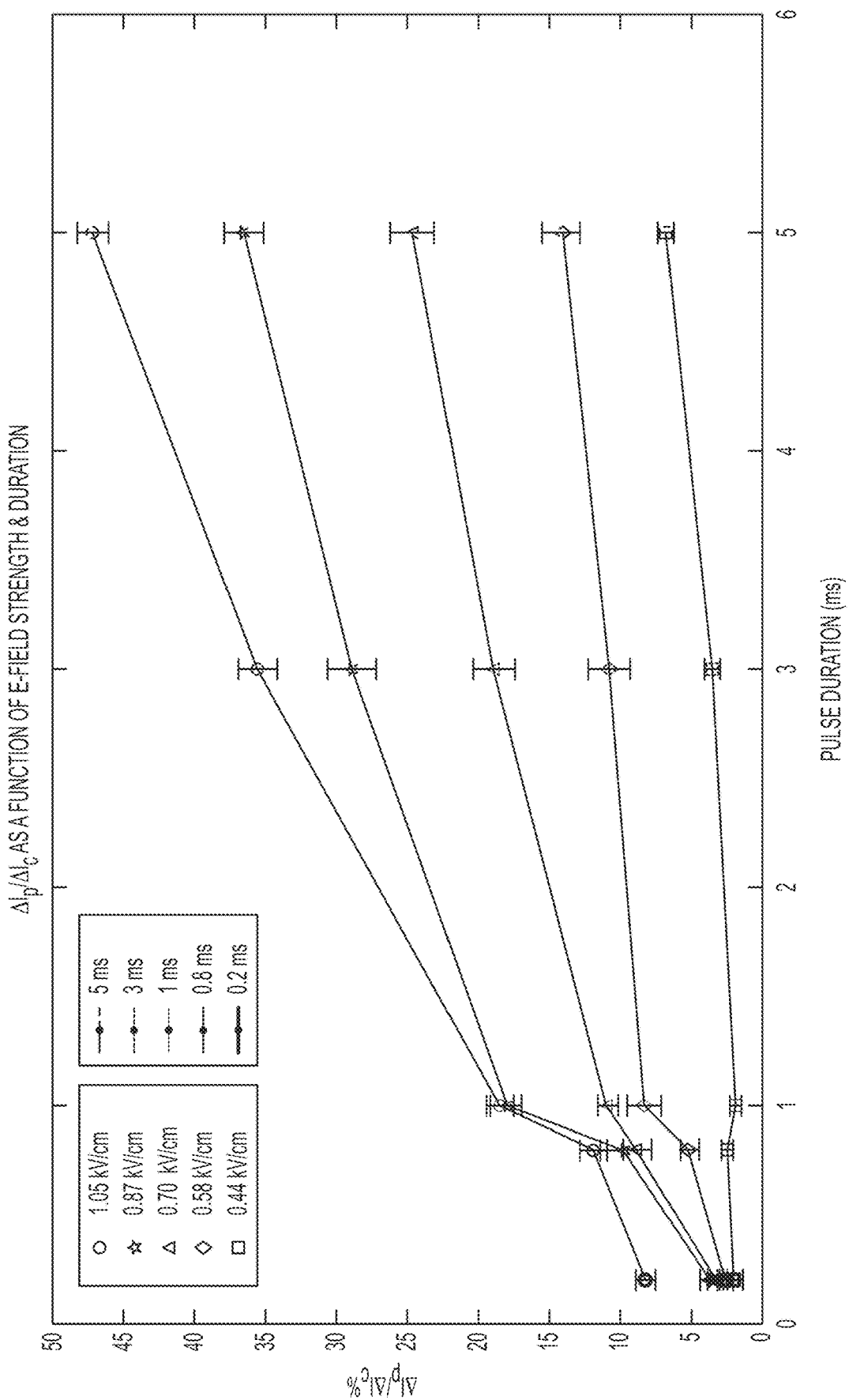
FIG. 11 shows a full characterization of the cell membrane response as a function of both electric-field strength and duration, according to an embodiment.

By varying the strength and duration of the electroporation pulse, we demonstrate changes in the cell impedance that are characteristic of the degree of cell-membrane permeabilization. As shown in FIG. 10, the measured cell current responses for five representative cells are superimposed at the time of pulse application. By keeping the electric field constant at 1.05 kV/cm while altering the pulse durations from 0 to 5.0 ms, a longer pulse duration is seemed to create a greater jump in current between the electrodes, indicating a higher degree of membrane permeabilization. A full characterization of the cell-membrane response as a function of both electric-field strength and duration is shown in FIG. 11. To account for cell-to-cell variations due to size differences, the change in the permeabilization current from the cell baseline ($\Delta I_p$) was first normalized by the total cell-current displacement ($\Delta I_c$) and expressed as a percentage increase from the detected cell-current baseline. When plotted as a function of pulse duration, a strong dependency was found between the normalized permeabilization current ($\Delta I_p/\Delta I_c$) and the pulse duration, for a given electric-field strength, with longer pulse durations leading to greater permeabilization. A strong dependence on electric-field magnitude was also observed when different strengths are applied for the same pulse duration, with stronger electric fields leading to greater permeabilization. For electric fields ranging from 0.58 to 1.05 kV/cm, we observed a rapid transition in the permeabilization signal occurring when the pulse duration reaches and exceeds 1.0 ms. Because the system allows for continuous flow and dynamic measurements of current, at least 200 cells were measured for each pulse condition, amounting to an analysis of 5,000 individual cells.

Permeabilization Validation—Propidium Iodide Fluorescence Tracking

Figure 12:
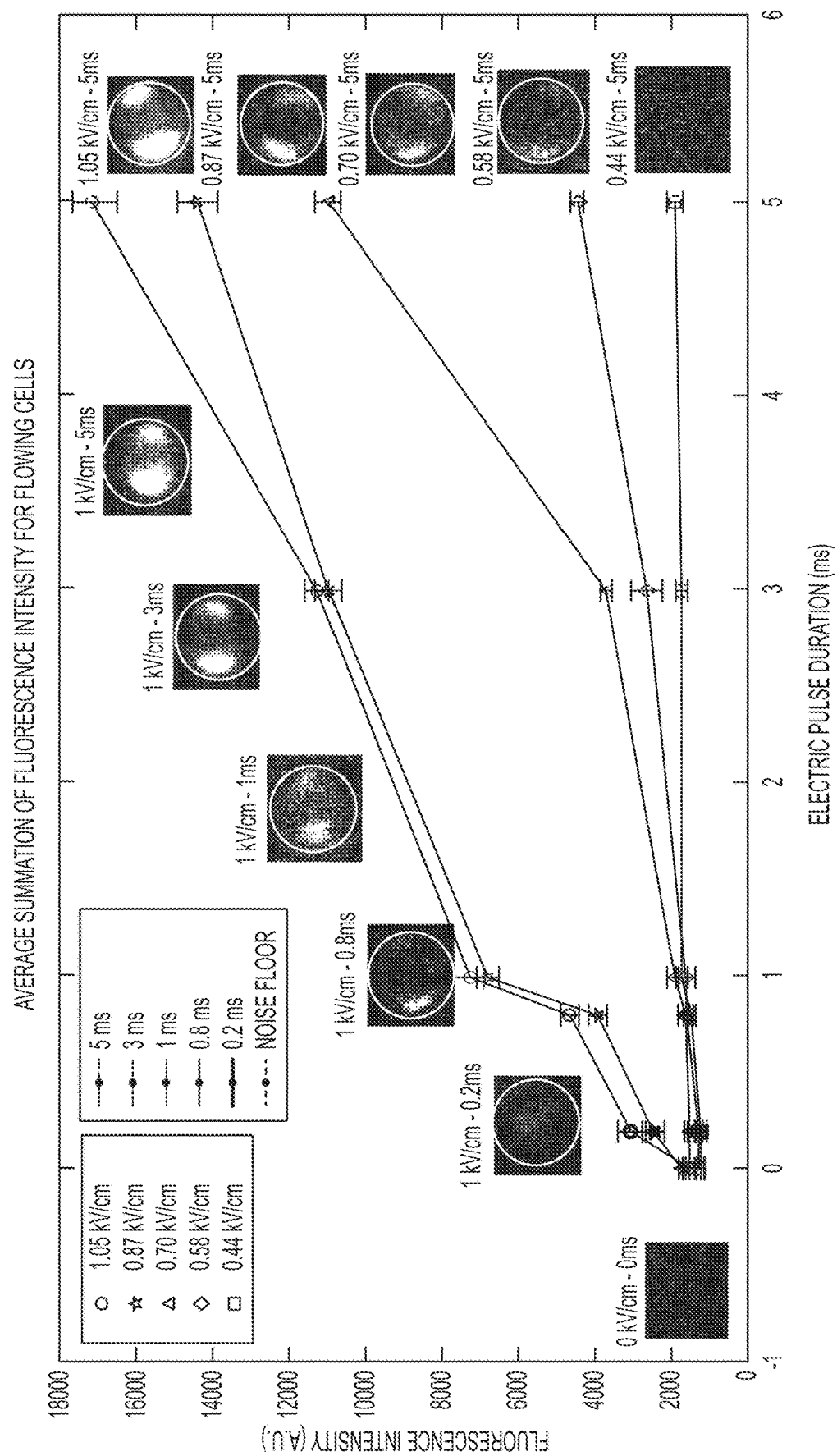
FIG. 12 shows a characterization of the cell membrane response as a function of both electric-field strength and duration together with optical propidium iodide fluorescence verification, according to an embodiment.

Electrically observed cell-membrane permeabilization was also verified optically by recording changes in fluorescence intensity that occur upon binding of PI to intercellular nucleic acids (FIG. 12). An optical camera was synchronized with the lock-in amplifier sensor to capture a sequence of images of the pulsed cell following each pulse application. These images were then evaluated for fluorescence intensity on an individual cell basis. Larger pulse strengths and durations lead to greater cell-membrane permeabilization, which in turn permit more PI entry through the porated cell membrane to bind with the nucleic acids in the cytoplasmic space, resulting in elevated fluorescence intensity.

A higher pulsing threshold is needed to produce optically distinguishable fluorescence intensities, due to the greater sensitivity of the electrical system. Optically, pulse durations longer than 1.0 ms were required to reliably correlate the degree of cell-membrane permeabilization to the electrical parameters. For instance, a significant jump in fluorescence intensity was observed after the 0.8 ms pulse duration consistent with the electrical measurements of the permeabilization signal. This relationship is further verified by plotting the electrical-permeabilization signal ($\Delta I_p/\Delta I_c$) versus fluorescence intensity for all pulse strengths and durations, which demonstrates that a linear and dependent relationship exists between the degree of membrane pore opening and the amount of PI delivered inside the cell. A large degree of poration is marked by a higher $\Delta I_p/\Delta I_c$ value, which corresponds to a greater extent of PI fluorescence intensity measured inside the treated cells. These data show a direct correlation between the amount of PI delivery and degree of membrane permeabilization, both of which are proportional to the electric-pulse parameters.

Cell Viability Study—Collection

Figure 13:
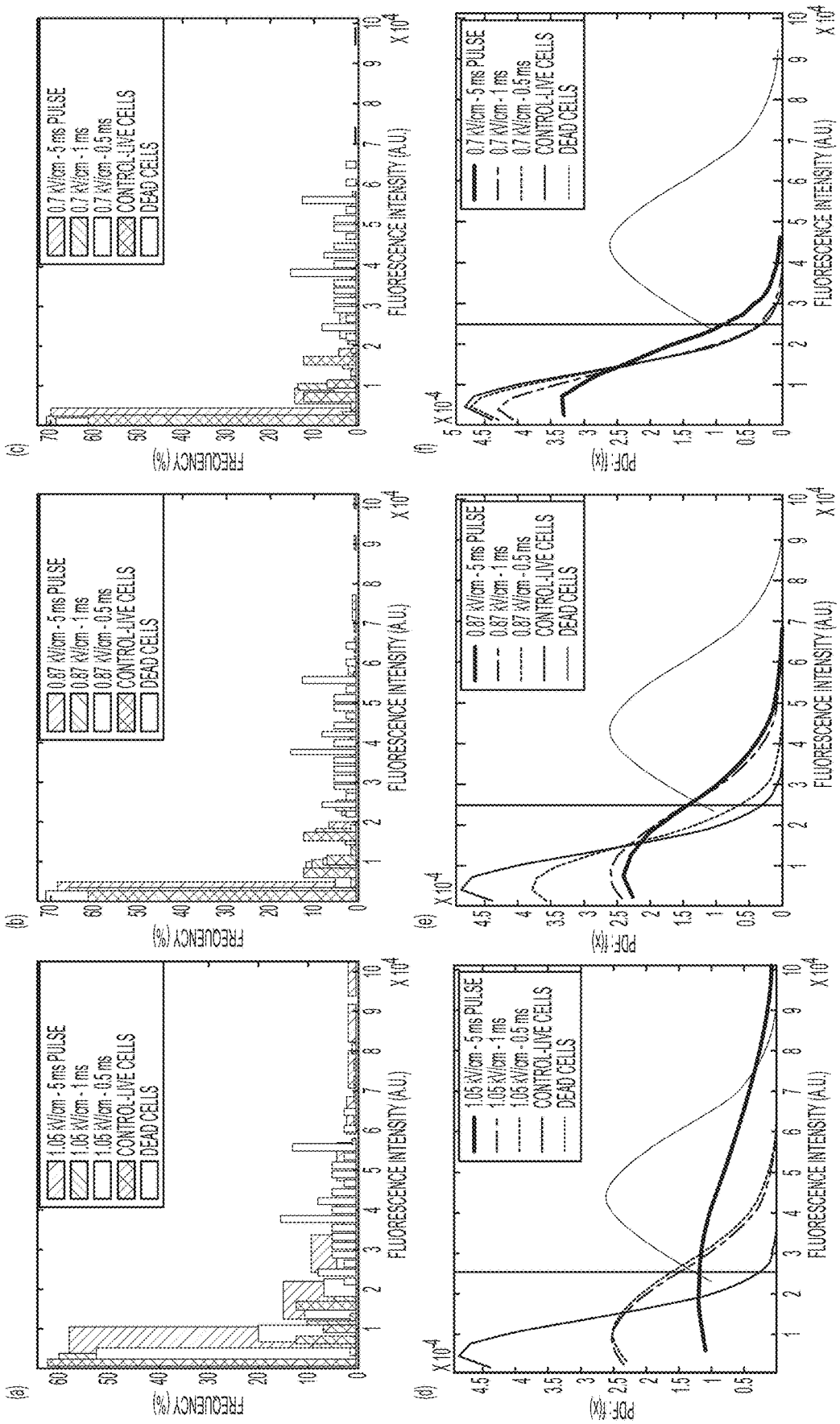
FIGS. 13A-13F show histograms of cell populations of cell populations treated with various electric-field strength and duration parameters, according to an embodiment.
Figure 14:
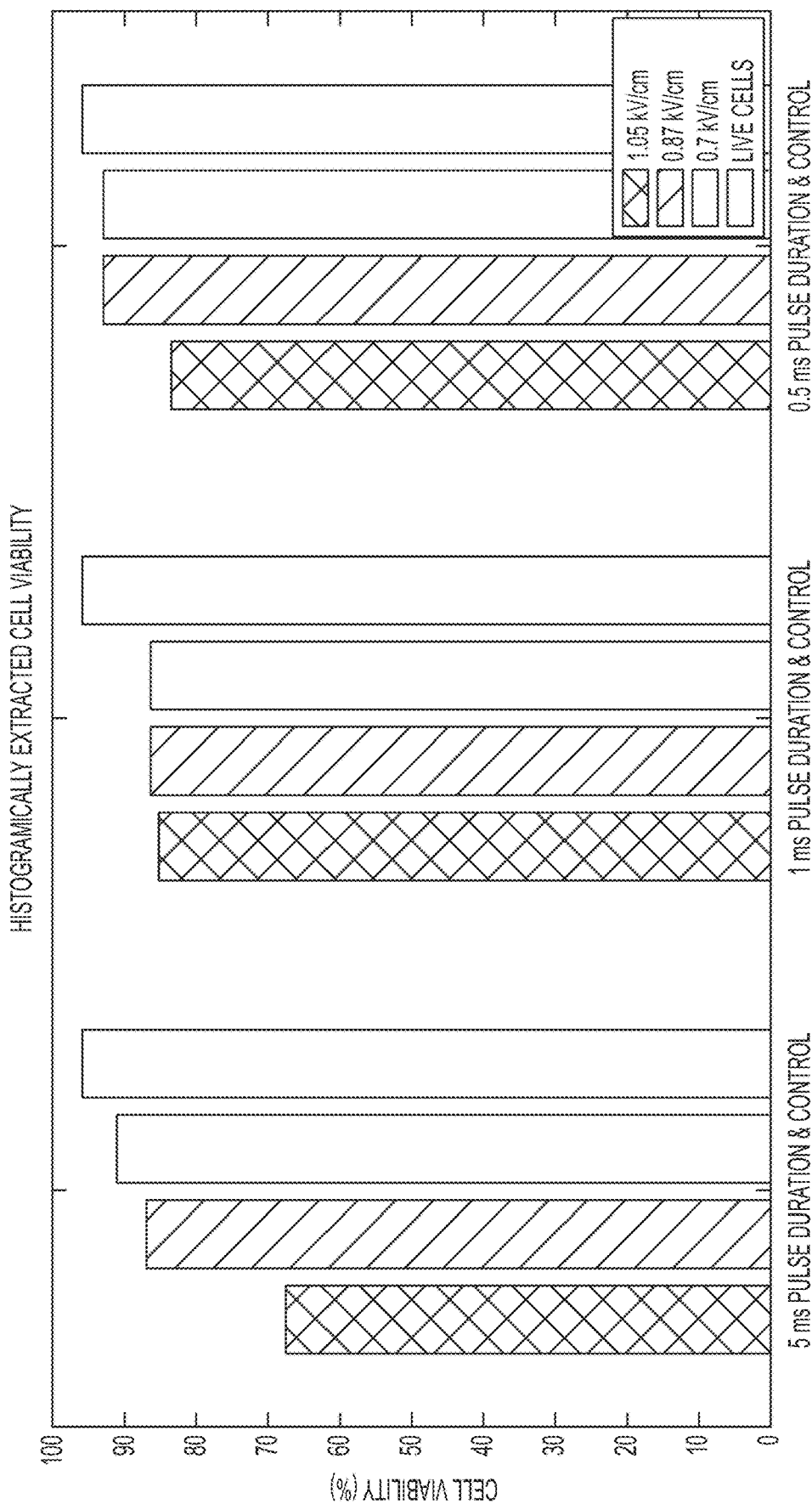
FIG. 14 shows the viability of cells for various electroporation conditions, according to an embodiment.

The viability of single cells undergoing a prescribed electroporation treatment was also correlated with the electroporation-pulse parameters through 7AAD staining. Cells were recovered 20 minutes after being exposed to the electroporation pulse so that viable cells had time for membrane resealing. We found that the combination of the highest electric-field strength (1.05 kV/cm) and pulse duration (5 ms) caused the greatest shift towards the distribution from the dead cells. This is expected since the strong electroporation treatment was more likely to irreversibly damage the cell membrane, hindering resealing. Decreasing the pulse strength or duration reduces the magnitude of the shift. All cells that underwent electroporation treatment at 0.7 kV/cm retained a comparable fluorescence to that of control live cells, indicating complete resealing of the cell membrane within 20 minutes post-permeabilization. A viability threshold was determined for each of the cell populations by calculating the 95% confidence lower bound of the mean fluorescence intensity for the dead-cell population, as shown by the vertical lines in FIGS. 13D-13F. FIG. 14 shows the viability of cells for each electroporation condition. The overall cell viability decreases monotonically with both the electric-field strength and pulse duration. A stronger pulsing condition was more likely to cause irreversible cell-membrane damage leading to cell death, whereas cells treated with moderate conditions (0.7 kV/cm) likely recovered, showing a higher population viability.

The above-disclosed features and functions, as well as alternatives, may be combined into many other different systems or applications. Various presently unforeseen or unanticipated alternatives, modifications, variations or improvements may be made by those skilled in the art, each of which is also intended to be encompassed by the disclosed embodiments.

What is claimed is:

1. A system for electroporating a biological cell, the system comprising:
    a microfluidic channel adapted to receive a flow of a plurality of biological cells in a buffer solution, wherein the microfluidic channel comprises a detection area;
    a pair of electrodes adapted to apply an electrical field across the detection area;
    a signal generator, wherein the signal generator is capable of generating a first signal, and a second signal through the electrodes, wherein the first signal is a cell detection signal and the second signal is a permeabilization signal;
    a sensor, wherein the sensor is adapted to continuously monitor an impedance value of the detection area; and
    a controller, wherein the controller is adapted to:
        determine that a single one of the plurality of biological cells has entered the detection area by monitoring the impedance value of the detection area increasing over a baseline threshold in the presence of the first signal, and
        in response to determining that the single one of the plurality of biological cells has entered the detection area, control the signal generator to generate the second signal.

2. The system of claim 1, wherein the signal generator is capable of generating the cell detection signal and the permeabilization signal simultaneously.

3. The system of claim 1, wherein the sensor comprises a lock-in amplifier.

4. The system of claim 1, wherein the sensor further comprises an imaging device capable of measuring fluorescence of a cell within the detection area.

5. The system of claim 1, wherein the microfluidic channel is adapted to hydrodynamically focus the flow of a plurality of biological cells through the detection area.

6. The system of claim 1, wherein the system further comprises a second microfluidic channel adapted to receive a flow of buffer without cells, and wherein the second microfluidic channel comprises a second detection area.

7. The system of claim 6, wherein the sensor is adapted to detect an impedance value of the second detection area, the impedance value of the second detection area providing a reference signal for determining that the single one of the plurality of biological cells has entered the detection area.

8. The system of claim 1, wherein the signal generator unit is further capable of generating a third signal that is a delivery signal that causes delivery of a molecule into the single one of the plurality of cells within the detection area.

9. The system of claim 1, wherein the controller unit is further adapted to control the signal generator to generate the second signal that has a plurality of pulse parameters selected based on the monitored impedance value of the detection area and associated data from a trapped cell experiment or a mathematical model.

10. The system of claim 8, wherein the controller unit is further adapted to control the signal generator to:
    stop generation of the second signal upon monitoring the impedance value of the detection area rising to greater than a permeabilization threshold value; and
    generate the third electrical signal according to the impedance detected by the sensor.

11. The system of claim 8, wherein the controller is further adapted to control the signal generator to dynamically adjust at least one parameter of the delivery signal based on the monitored impedance value to allow delivery of the molecule without reaching excessive changes in impedance indicative of cell death.

12. The system of claim 11, wherein the controller is adapted to:
    determine whether the impedance value of the detection area is about equal to the permeabilization threshold value,
    wherein the controlling of the signal generator to adjust at least one parameter of the delivery signal to allow molecular delivery without reaching excessive changes in impedance indicative of cell death is in response to determining the impedance value of the detection area is not about equal to the permeabilization threshold value.

13. The system according to claim 11, wherein the at least one parameter of the delivery signal is selected from the group of: electric field amplitude, pulse duration, pulse train frequency, duty cycle, and number of cycles.

14. The system of claim 8, wherein the controller is adapted to control the signal generator to generate the third signal that has a plurality of pulse parameters selected based on the monitored impedance value of the detection area and associated data from a trapped cell experiment or a mathematical model.

15. The system of claim 8, wherein the controller unit is adapted to control the signal generator to stop generation of the third signal in response to at least one of the following:
    determining that the monitored impedance value is less than the threshold impedance indicating that that the single one of the plurality of biological cells has exited the detection area; or
    determining that the monitored impedance value is equal to a viability threshold for over-exposure.

16. The system of claim 1, wherein the flow of the plurality of biological cells is continuous.

17. The system according to claim 10, wherein the permeabilization threshold value is determined experimentally or using a mathematical model.

18. The system according to claim 10, wherein the permeabilization threshold value corresponds to an optimal cell permeabilization that does not cause cell death.

19. The system according to claim 1, wherein the sensor is adapted to, upon determining that the single one of the plurality of biological cells has entered the detection area, operate at a sensing frequency range that is configured to sense a variation in impedance of the single one of the plurality of cells due to permeabilization, the sensing frequency range being about 1 KHz to about 10 KHz.

* * * * *

UNITED STATES PATENT AND TRADEMARK OFFICE
CERTIFICATE OF CORRECTION

| | | |
|---|---|---|
| PATENT NO. | : 10,927,333 B2 | Page 1 of 1 |
| APPLICATION NO. | : 15/757566 | |
| DATED | : February 23, 2021 | |
| INVENTOR(S) | : Jeffrey Zahn et al. | |

It is certified that error appears in the above-identified patent and that said Letters Patent is hereby corrected as shown below:

In the Specification

At Column 1, Line number 17, reads:
"The present invention was partly sponsored by the National Science Foundation (NSF) through the IDBR Award #1959918 and the CBET Award #0967598."

Should read:
--This invention was made with government support under grant numbers CBET0967598 and 1353918 awarded by the National Science Foundation. The government has certain rights in the invention.--

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*